(12) United States Patent
Abhari et al.

(10) Patent No.: US 8,969,259 B2
(45) Date of Patent: Mar. 3, 2015

(54) BIO-BASED SYNTHETIC FLUIDS

(71) Applicant: Syntroleum Corporation, Tulsa, OK (US)

(72) Inventors: Ramin Abhari, Bixby, OK (US); E. Gary Roth, Bristow, OK (US); Peter Z. Havlik, Tulsa, OK (US); H. Lynn Tomlinson, Tulsa, OK (US)

(73) Assignee: Reg Synthetic Fuels, LLC, Ames, IA (US)

( * ) Notice: Subject to any disclaimer, the term of this patent is extended or adjusted under 35 U.S.C. 154(b) by 0 days.

(21) Appl. No.: 13/871,972

(22) Filed: Apr. 26, 2013

(65) Prior Publication Data

US 2014/0303057 A1 Oct. 9, 2014

Related U.S. Application Data

(60) Provisional application No. 61/809,183, filed on Apr. 5, 2013.

(51) Int. Cl.
*C09K 8/02* (2006.01)
*C09K 8/34* (2006.01)
*C09K 8/64* (2006.01)
*C10G 3/00* (2006.01)
(Continued)

(52) U.S. Cl.
CPC . *C10G 3/00* (2013.01); *C09K 21/08* (2013.01); *E21B 43/26* (2013.01)
USPC .......................................... 507/103; 507/203

(58) Field of Classification Search
CPC ............... C09K 8/34; C09K 8/64; C09K 8/02
USPC ................................................... 507/103, 203
See application file for complete search history.

(56) References Cited

U.S. PATENT DOCUMENTS 2,093,159 A 9/1937 Schmidt
2,163,563 A 6/1939 Schrauth
(Continued)

FOREIGN PATENT DOCUMENTS

CA 1313200 1/1993
CA 2149685 9/1999
(Continued)

OTHER PUBLICATIONS

Abhari et al., "New Routes to Ethylene," EEPC Seminar in Berlin, Germany, Oct. 20-22, 2010, pp. 1-38.
(Continued)

*Primary Examiner* — Ellen McAvoy
(74) *Attorney, Agent, or Firm* — Foley & Lardner LLP

(57) ABSTRACT

A method is provided involving altering the viscosity of bio-derived paraffins to produce a paraffinic fluid, where the altering step includes oligomerizing bio-derived paraffins, unsaturating bio-derived paraffins, chlorinating bio-derived paraffins, or a combination of any two or more thereof; the bio-derived paraffins are produced by hydrodeoxygenating a bio-based feed; the bio-based feed comprises bio-derived fatty acids, fatty acid esters, or a combination thereof; the bio-derived paraffins comprise n-paraffins; and the n-paraffins have a biodegradability of at least 40% after about 23 days of exposure to microorganisms. Also provided are methods of protecting a substance by applying a paraffinic fluid and a method of producing an orifice in a substrate by at least injecting a paraffinic fluid into the substrate.

24 Claims, 1 Drawing Sheet

(51) Int. Cl.
*C09K 21/08* (2006.01)
*E21B 43/26* (2006.01)

(56) References Cited

U.S. PATENT DOCUMENTS

| | | | |
|---|---|---|---|
| 2,482,760 A | 9/1949 | Goebel | |
| 2,482,761 A | 9/1949 | Goebel | |
| 2,664,429 A | 12/1953 | Goebel | |
| 2,793,220 A | 5/1957 | Barrett, et al. | |
| 2,915,447 A | 12/1959 | Arabian | |
| 3,144,404 A | 8/1964 | Tyson | |
| 3,363,022 A | 1/1968 | Harrison, et al. | |
| 3,496,099 A | 2/1970 | Bridge | |
| 3,505,418 A | 4/1970 | Jubin | |
| 3,903,191 A | 9/1975 | Pollitzer | |
| 3,979,470 A | 9/1976 | Firnhaber et al. | |
| 4,049,686 A | 9/1977 | Ringers et al. | |
| 4,151,072 A | 4/1979 | Nowack et al. | |
| 4,233,140 A | 11/1980 | Antonelli et al. | |
| 4,252,634 A | 2/1981 | Khulbe et al. | |
| 4,300,006 A | 11/1981 | Nelson | |
| 4,300,009 A | 11/1981 | Haag et al. | |
| 4,431,524 A | 2/1984 | Norman | |
| 4,432,865 A | 2/1984 | Norman | |
| 4,451,689 A | 5/1984 | Pasky | |
| 4,512,878 A | 4/1985 | Reid et al. | |
| 4,554,397 A | 11/1985 | Stern et al. | |
| 4,571,442 A | 2/1986 | Cosyns et al. | |
| 4,594,172 A | 6/1986 | Sie | |
| 4,698,185 A | 10/1987 | Dijkstra et al. | |
| 4,734,226 A | 3/1988 | Parker et al. | |
| 4,746,420 A | 5/1988 | Darian et al. | |
| 4,913,794 A | 4/1990 | Le et al. | |
| 4,937,051 A | 6/1990 | Graven et al. | |
| 4,960,960 A | 10/1990 | Harrison et al. | |
| 4,992,605 A | 2/1991 | Craig et al. | |
| 5,037,528 A | 8/1991 | Garwood et al. | |
| 5,093,535 A | 3/1992 | Harrison et al. | |
| 5,105,015 A | 4/1992 | Lin et al. | |
| 5,135,638 A | 8/1992 | Miller | |
| 5,146,022 A | 9/1992 | Buchanan et al. | |
| 5,239,096 A | 8/1993 | Rohdenburg et al. | |
| 5,292,428 A | 3/1994 | Harrison et al. | |
| 5,298,639 A | 3/1994 | Toeneboehn et al. | |
| 5,346,724 A | 9/1994 | Ohgake et al. | |
| 5,378,348 A | 1/1995 | Davis et al. | |
| 5,475,160 A | 12/1995 | Singleton et al. | |
| 5,502,077 A | 3/1996 | Breivik et al. | |
| 5,578,090 A | 11/1996 | Bradin | |
| 5,635,457 A * | 6/1997 | Van Slyke | 507/103 |
| 5,647,226 A | 7/1997 | Scaringe et al. | |
| 5,688,749 A | 11/1997 | Ibuki et al. | |
| 5,705,722 A | 1/1998 | Monnier et al. | |
| 5,851,338 A | 12/1998 | Pushaw | |
| 5,877,358 A | 3/1999 | Garton et al. | |
| 5,882,505 A | 3/1999 | Wittenbrink et al. | |
| 5,906,729 A | 5/1999 | Chou | |
| 6,034,037 A * | 3/2000 | Van Slyke | 507/103 |
| 6,054,415 A * | 4/2000 | Gee et al. | 507/103 |
| 6,096,690 A * | 8/2000 | Wittenbrink et al. | 507/103 |
| 6,123,835 A | 9/2000 | Ackerson et al. | |
| 6,150,575 A | 11/2000 | Angevine et al. | |
| 6,159,907 A * | 12/2000 | Van Slyke | 507/203 |
| 6,185,742 B1 | 2/2001 | Doherty | |
| 6,187,903 B1 | 2/2001 | Elsasser et al. | |
| 6,190,535 B1 | 2/2001 | Kalnes et al. | |
| 6,203,695 B1 | 3/2001 | Harle et al. | |
| 6,255,256 B1 * | 7/2001 | Van Slyke | 507/103 |
| 6,402,935 B1 | 6/2002 | Kalnes | |
| 6,420,618 B1 | 7/2002 | Berlowitz et al. | |
| 6,455,474 B1 | 9/2002 | Wittenbrink et al. | |
| 6,475,960 B1 | 11/2002 | Berlowitz et al. | |
| 6,518,473 B2 | 2/2003 | Miller et al. | |
| 6,574,971 B2 | 6/2003 | Suppes | |
| 6,613,404 B2 | 9/2003 | Johnson | |
| 6,638,418 B1 | 10/2003 | Kalnes et al. | |
| 6,660,812 B2 | 12/2003 | Kuechler et al. | |
| 6,787,022 B1 | 9/2004 | Berlowitz et al. | |
| 6,806,237 B2 | 10/2004 | O'Rear | |
| 6,833,064 B2 | 12/2004 | Berlowitz et al. | |
| 6,846,778 B2 | 1/2005 | Johnson et al. | |
| 6,855,410 B2 | 2/2005 | Buckley | |
| 7,071,150 B2 | 7/2006 | Genuyt et al. | |
| 7,081,437 B2 | 7/2006 | Patel et al. | |
| 7,232,935 B2 | 6/2007 | Jakkula et al. | |
| 7,288,685 B2 | 10/2007 | Marker | |
| 7,311,814 B2 | 12/2007 | Guyomar et al. | |
| 7,326,817 B2 | 2/2008 | Dunlop et al. | |
| 7,429,553 B2 | 9/2008 | Dunlop et al. | |
| 7,485,602 B2 * | 2/2009 | Kirsner et al. | 507/103 |
| 7,511,181 B2 | 3/2009 | Petri et al. | |
| 7,550,634 B2 | 6/2009 | Yao et al. | |
| 7,691,159 B2 | 4/2010 | Li | |
| 7,718,051 B2 | 5/2010 | Ginosar et al. | |
| 7,718,580 B2 * | 5/2010 | Saruwatari et al. | 507/103 |
| 7,754,931 B2 | 7/2010 | Monnier et al. | |
| 7,816,570 B2 | 10/2010 | Roberts et al. | |
| 7,836,722 B2 | 11/2010 | Magill et al. | |
| 7,846,323 B2 | 12/2010 | Abhari et al. | |
| 7,851,663 B2 | 12/2010 | Abhari | |
| 7,928,273 B2 | 4/2011 | Bradin | |
| 7,960,597 B2 | 6/2011 | Miller | |
| 7,967,973 B2 * | 6/2011 | Myllyoja et al. | 208/64 |
| 7,968,757 B2 | 6/2011 | Abhari et al. | |
| 7,982,076 B2 | 7/2011 | Marker et al. | |
| 7,998,339 B2 * | 8/2011 | Myllyoja et al. | 208/18 |
| 8,003,836 B2 | 8/2011 | Marker et al. | |
| 8,022,258 B2 | 9/2011 | Myllyoja et al. | |
| 8,026,401 B2 | 9/2011 | Abhari et al. | |
| 8,187,344 B2 | 5/2012 | Jakkula et al. | |
| 8,212,094 B2 | 7/2012 | Myllyoja et al. | |
| 8,231,804 B2 | 7/2012 | Abhari | |
| 8,278,492 B2 | 10/2012 | Myllyoja et al. | |
| 2002/0062053 A1 | 5/2002 | Berlowitz et al. | |
| 2004/0055209 A1 | 3/2004 | Jakkula et al. | |
| 2004/0067856 A1 | 4/2004 | Johnson et al. | |
| 2004/0170806 A1 | 9/2004 | Hittle et al. | |
| 2004/0230085 A1 | 11/2004 | Jakkula et al. | |
| 2005/0150815 A1 | 7/2005 | Johnson et al. | |
| 2006/0161032 A1 | 7/2006 | Murzin et al. | |
| 2006/0186020 A1 | 8/2006 | Gomes | |
| 2006/0199984 A1 | 9/2006 | Kuechler et al. | |
| 2006/0207166 A1 | 9/2006 | Herskowitz et al. | |
| 2006/0264684 A1 | 11/2006 | Petri et al. | |
| 2007/0006523 A1 | 1/2007 | Myllyoja et al. | |
| 2007/0010682 A1 | 1/2007 | Myllyoja et al. | |
| 2007/0026012 A1 | 2/2007 | DeLisa et al. | |
| 2007/0131579 A1 | 6/2007 | Koivusalmi et al. | |
| 2007/0161832 A1 | 7/2007 | Myllyoja et al. | |
| 2007/0170091 A1 | 7/2007 | Monnier et al. | |
| 2007/0260102 A1 | 11/2007 | Duarte Santiago et al. | |
| 2009/0077866 A1 | 3/2009 | Kalnes et al. | |
| 2012/0251424 A1 | 10/2012 | Havlik et al. | |
| 2013/0012745 A1 * | 1/2013 | Knuuttila et al. | 585/240 |

FOREIGN PATENT DOCUMENTS

| | | |
|---|---|---|
| CZ | 283575 | 5/1998 |
| DE | 41 16 905 | 8/1992 |
| EP | 0 412 785 | 2/1991 |
| EP | 0 794 241 | 3/1997 |
| EP | 1 396 531 A2 | 3/2004 |
| EP | 1 728 844 | 12/2006 |
| FI | 72435 | 2/1987 |
| FI | 73367 | 6/1987 |
| FI | 89073 | 4/1993 |
| FI | 95391 | 1/1996 |
| GB | 1 061 644 | 3/1967 |
| GB | 2 090 611 | 7/1982 |
| IE | 921671 | 12/1995 |
| JP | 59-108088 | 6/1984 |
| SE | 9700149 | 8/1997 |
| SE | 520633 | 8/2003 |
| WO | WO-00/11117 | 3/2000 |

(56) References Cited

FOREIGN PATENT DOCUMENTS

| WO | WO-00/29512 | 5/2000 |
|---|---|---|
| WO | WO-01/49812 | 7/2001 |
| WO | WO-03/022960 | 3/2003 |
| WO | WO-03/022960 A2 | 3/2003 |
| WO | WO-2004/026161 | 4/2004 |
| WO | WO-2004/104142 | 12/2004 |
| WO | WO-2005/026297 | 3/2005 |
| WO | WO-2006/100584 | 9/2006 |
| WO | WO-2007/003708 A1 | 1/2007 |
| WO | WO-2007/063874 | 6/2007 |
| WO | WO-2007/068795 | 6/2007 |
| WO | WO-2008/027699 | 3/2008 |
| WO | WO-2008/054442 | 5/2008 |
| WO | WO-2008/058664 | 5/2008 |
| WO | WO-2008/067627 | 6/2008 |
| WO | WO-2009/085686 | 7/2009 |
| WO | WO-2009/117337 | 9/2009 |
| WO | WO-2009/151692 | 12/2009 |

OTHER PUBLICATIONS

Ali et al., "Fuel Properties of Tallow and Soybean Oil Esters," JAOCS, 1995, vol. 72, No. 12.
Antoniassi, R. et al, "Pretreatment of Corn Oil for Physical Refining," JAOCS, vol. 75, No. 10, 1998, pp. 1411-1415.
Arroyo et al., "Hydrocracking and isomerization of n-paraffin mixtures and a hydrotreated gasoil on Pt/ZSM-22: confirmation of pore mouth and key013lock catalysis in liquid phase," Applied Catalysis A: General 192, 2000, pp. 9-22.
ASTM International, "Standard Specification for Diesel Fuel Oil", Designation: D975-12, printed Nov. 9, 2012, 26 pages.
Batts et al., "A Literature Review on Fuel Stability Studies with Particular Emphasis on Diesel Oil", Energy & Fuels, 1991, vol. 5, pp. 2-21.
Bergerioux, C. et al, "Determination of Trace Element Pathways in a Petroleum Distillation Unit by Instrumental Neutron Activation Analysis," Journal of Radioanalytical Chemistry, vol. 54, No. 1-2, 1979, pp. 255-265.
Burch et al., "Melting-Point Models of Alkanes", J. Chem. Eng. Data 2004, 49, 858-863.
Canada Centre for Mineral and Energy Technology, "New Process Yields Cleaner Diesel", Canmet'95: New Directions, 1995, p. 14.
Canakci et al., "Biodiesel Production from Oils and Fats with High Free Fatty Acids", Transactions of the ASAE, 2001, vol. 44(6), pp. 1429-1436.
Clements, L.D., "Blending Rules for Formulating Biodiesel Fluid.", Proceedings of the Third Liquid Fuels Conference, Sep. 15-17, 1996, pp. 44-53.
Cmolik et al., "Effects of plant-scale alkali refining and physical refining on the quality of rapeseed oil", Eur. J. Lipod Sci. Technol. 2000, 15-22.
Cooper et al., "Production of Swedish Class I Diesel Using Dual-Stage Process", Catalytic Hydroprocessing of Petroleum and Distillates, based on Proceedings of the AIChE Spring National Meeting, Houston, Texas, Mar. 28-Apr. 1, 1993, 279-290.
Corma, et al., "Transformation of Alkanes on Solid Acid and Bifunctional Catalysts", Catalytic Activation and Functionalisation of Light Alkanes: Advances and Challenges, Editors E.G. Derouane et al., 1998, Netherlands: Kluwer Academic Publishers, vol. 44, pp. 35-74.
Criterion, "Technical Bulletin: CRITERION* Hydrotreating Catalyst In-Situ Presulphiding Guidelines—Liquid Phase (Preferred method)—Gase Phase (alternative method)" Criterion Catalysts, Aug. 1998, 1-9.
Deem, A.G. et al, "Catalytic Poisoning in Liquid-Phase Hydrogenation," Industrial and Engineering Chemistry, vol. 33, No. 11, Nov. 1941, pp. 1373-1376.
Del Gallo et. al. "Comparison of the Effects of Nitrogen Poisoning on Molybdenum Oxycarbide and Pt/B-Zeolite Catalysts in the Isomerization of n-Heptane," Ind. Eng. Chem. Res., 1996, vol. 35, No. 10, pp. 3302-3310.

Derrien et al., "The IFP Selective Hydrogenation Process", Chemical Engineering Process, vol. 70, No. 1, Jan. 1974, 74-80.
Doty, D.M. (1971). "Removal of Polyethylene and Other Polymeric Materials from Rendered Animal Fat." The Director's Digest, Fats and Proteins Research Foundation, Inc., 90, 4 pgs.
Dynamic Fuels, "About", http://www.dynamicfuelsllc.com/. Accessed Nov. 12, 2012, 8 pages.
Dynamic Fuels, "Compare", http://www.dynamicfuelsllc.com/. Accessed Nov. 12, 2012, 7 pages.
Dynamic Fuels, "Frequently Ask Questions," http://dynamicfuelsllc.com/wpnews/frequently-ask-questions/, Accessed Nov. 12, 2012, 4 pages.
Edgar et al., "Analysis is key to hydrotreater troubleshooting", Oil & Gas Journal, vol. 82, issue 23, Jun. 4, 1984, 67-70.
Egeberg et al., "Hydrotreating in the Production of Green Diesel," Digital Refining, Apr. 2010, 13 pages; Available for download at http://www.digitalrefining.com/article/1000156,Hydrotreating_in_the_production_of_green_diesel.html#.UcSCEKybWVo.
Egeberg, et al., "Novel Hydrotreating Technology for Production of Green Diesel," 14th European Refining Technology Conference, Berlin, Germany, Nov. 9-11, 2009, 21 pages.
Erickson et al., "Soybean Oil Modern Processing and Utilization", American Soybean Association, 1990, 20 pages.
Feng et al., "Chemical Composition of Tall-Oil Based Cetane Enhancer for Diesel Fuels", First Biomass Conference of the Americas: Energy, Environment, Agriculture, and Industry, Aug. 30-Sep. 2, 1993. 14 pages.
Filho et al., Catalytic Conversion of *Hevea brasiliensis* and *Virola sebifera* Oils to Hydrocarbon Fuels, JAOCS, vol. 69, No. 3, Mar. 1992, 266-271.
Galeana et al., "Thermodynamics of Wax Precipitation in Petroleum Mixtures," AIChE Journal, 1996, vol. 42, No. 1, pp. 239-248.
Galperin, "Hydroisomerization of N-decane in the presence of sulfur and nitrogen compounds," Applied Catalysis A: General, 209, 2001 pp. 257-268.
Garrido et al., "Concentrations of Metal in vegetable edible oils", Food Chemistry, vol. 50, 1994, 237-243.
Goering et al., "Fuel Properties of Eleven Vegetable Oils," Transactions of the ASAE, 1982, pp. 1472-1477, 1483.
Goodrum et al., "Rheological Characterization of Yellow Grease and Poultry Fat," JAOCS, 2002, vol. 79, No. 10, pp. 961-964.
Groschen, R., "Overview of: The Feasibility of Biodiesel from Waste/Recycled Greases and Animal Fats", Marketing Services Division, Minnesota Department of Agriculture, Oct. 2002, 28 pages.
Gusmao et al., "Utilization of Vegetable Oils as an Alternative Source for Diesel-Type Fuel," Catalysis Today, 5, 1989, pp. 533-544.
Herrera et al., "Catalyst Selection for Hydrotreating Diesel Fuel from Residue Hydrocracking", ACS Preprints, 1992, vol. 37, No. 4, pp. 1855-1863.
Hill, C., An Introduction to Chemical Engineering Kinetics & Reactor Design, John Wiley & Sons, Inc., 1977, pp. 349-380, 382-387.
Holmgren, et al., "New Developments in Renewable Fuels Offer More Choices", Hydrocarbon Processing, Sep. 2007, pp. 67-72.
Iki, et al., "Applicability of Hydrogenated Palm Oil for Automotive Fuels", 16th Saudi Arabia-Japen Joint Symposium, Dhahran, Saudi Arabia, Nov. 5-6, 2006, 10 pages.
Kalnes, et al.; Provisional U.S. Appl. No. 60/973,788, entitled "Production of Diesel Fuel from Biorenewable Feedstocks", filed Sep. 9, 2007.
Kent, J., "Table 8.2", Riegel's Handbook of Industrial Chemistry, 9th Edition, 1992, pp. 278-279.
Kirk-Othmer, "Gravity Concentration to Hydrogen Energy", Encyclopedia of Chemical Technology, Third Edition, vol. 12, Copyright 1980 by John Wiley & Sons, Inc., 931-937.
Klimisch et al., "Paraffinic Naphthas", American Petroleum Institute, May 20, 2003, 41 pages.
Kriz, et al., "Catalysts for the Isomerization of C7 Paraffins," Ind. Eng. Chem. Res., 1998, 37:4560-4569.
Levenspiel, O., Chemical Reaction Engineering, Third Edition, John Wiley & Sons, Inc., 1999, pp. 207-239.
Lewis, R.J., Hawley's Condensed Chemical Dictionary, 12th Edition, 1993, p. 907.

(56) References Cited

OTHER PUBLICATIONS

Long et al., "Noble Metal (Pt, Rh, Pd) Promoted Fe-ZSM-5 for Selective Catalytic Oxidation of Ammonia to N2 at Low Temperatures", Catalysis Letters, Mar. 2002, vol. 78, Nos. 1-4, pp. 353-357.
MacDonald, "Fuel From Fats," enerG Alternative Sources Magazine, Sep./Oct. 2011, 4 pages.
Mag, T., "Canola Seed and Oil Processing", Canola Council of Canada, 1994, 6 pages.
Mansfield Fuels, "Norfolk Southern Pens Deal with Dynamic Fuels and Mansfield Oil", http://www.mansfieldoil.com/latest-news-a-press/524-norfolk-southern-pens-deal-with-dynamic-fueis-and-mansfield-oil.html, Accessed Nov. 12, 2012, 2 pages.
Marker, T.L., "Opportunities for Biorenewables in Oil Refineries Final Technical Report" submitted to U.S. Department of Energy, Apr. 2005, 60 pages.
Miller, "Studies on Wax Isomerization for Lubes and Fuels, Zeolited and Related Microporous Materials: State of the Art in 1994," Studies in Surface Science and Catalysts, 1994, vol. 84, pp. 2319-2326.
Mirante et al., "Cloud point prediction of fuels and fuel blends," Fluid Phase Equilibria 180, 2001, pp. 247-255.
Moyse, "Graded Catalyst Systems to Combat Bed-Fouling Problems", Haldor Topsoe, Inc. 1996, 16 pages.
Plantenga et al., "Specialized guard-bed technology can improve resid unit operation", Oil & Gas Journal, Oct. 21, 1991, 74-78.
Pope et al., "A Study of Catalyst Formulations for Isomerization of C7 Hydrocarbons", Applied Catalysis A: General 233, 2002, pp. 45-62.
Prakash, "A Critical Review of Biodiesel As A Transportation Fuel in Canada", Mar. 25, 1998, 163 pages.
Proctor & Gamble, "Better Rendering, A Manual Prepared by Proctor & Gamble", 2nd Ed., 1967, pp. ix-xi, 1-21.
Przybylski, R., "Canola Oil: Physical and Chemical Properties", Canola Council of Canada, 1998, 12 pages.
Rahimi et al., "Effect of Hydrotreating on the Stability of Synthetic Crude from Western Canada,"Symposium on Stability and Oxidation Chemistry of Fuels, Dallas, Spring 1998, ACS Fuels 43 (1), pp. 13-17; Available for download athttp://web.anl.gov/PCS/acsfuel/preprint%20archive/43_1_DALLAS_03-98.htm.
Sanford et al., "Improved Catalyst Loading Reduces Guard Reactor Fouling", Oil & Gas Journal, Dec. 19, 1988, pp. 35-41.
Sharma, S.D., et al.; "Latent Heat Storage Materials and Systems: A Review"; International Journal of Green Energy; 2:1-56; 2005.
Simacek, et al., "Hydroprocessed rapeseed oil as a source of hydrocarbon-based biodiesel", Fuel 88, 2009, 456-460.
Smejkal, et al., "Thermodynamic balance in reaction system of total vegetable oil hydrogenation", Chemical Engineering Journal 146 (2009) 155-160.
Soveran et al., "The Effect on Diesel Engine Emissions with High Cetane Additives From Biomass Oils," Proc. American Chemical Society (Division of Fuel Chemistry) Meeting San Francisco, CA, Apr. 1992, pp. 74-85.
Spataru, "AGTNAE (AGricultural ceTANE): An Economically Viable Bioenergy Product for Compression Ignited Engines", Fuel Chemistry Division Preprints, 2002, vol. 47(1), p. 365.
Spataru, "Is There a Future for Yellow Grease as a Fuel Additive?," Render, Feb. 2001, pp. 12-14.
Spataru, et al., "AGRANE (AGricultural ceTANE): An economically viable bioenergy product for compression ignited engines," 5th International Biomass Conference of the Americas Sep. 21, 2001, 2 pages.
Stork, W.H.J., "Molecules, catalysts and reactors in hydroprocessing of oil fractions", Hydrotreatment and Hydrocracking of oil fractions, 1997 Elsevier Science B.V., 41-67.
Stumborg et al., "Hydroprocessed Vegetable Oils for Diesel FuelImprovement." Bioresources Technology, 1996, vol. 56, pp. 13-18.
Syntroleum webpage, "Bio-Synfining—Dynamic Fuels Plant"; http://www.b2i.us/profiles/investor/fullpage.asp?BzID=2029&to=cp&Nav=O&LangID=1&s=0&ID=11923 , Accessed Nov. 21, 2012, 4 pages.
Table 4a. U.S. Crude Oil and Liquid Fuels Supply, Consumption and Inventories, Dec. 2012, 1 pp.
Taylor et al., Modern Advanced Control Pays Back Rapidly, Hydrocarbon Processing, Sep. 2000 issue, pp. 47-50.
Tyson et al., "Biomass Oil Analysis: Research needs and Recommendations," NREL Technical Report, Jun. 2004, 116 pages.
U.S. Dept. Of Agriculture—Oilseeds: World Markets and Trade, "Soybean Oil and Palm Oil Account for an Increasing Share of Word Vegetable Oil Consumption", (2003), 27 pages.
U.S. Natural Gas Wellhead Price data and graph from U.S. Energy Information Administration, released Nov. 30, 2012, 1 pp; Available for download at http://www.eia.gov/dnav/ng/ng_pri_sum_dcu_nus_m.htm.
Vajo, et al., "Steady-State Decomposition of Ammonia on the Pt(110)-(1×2) Surface", The Journal of Physical Chemistry, 1986, vol. 90, No. 24, pp. 6531-6535.
Wong et al., "Conversion of Vegetable Oils and Animal Fats Into Paraffinic Cetane Enhancers for Diesel Fuels," Second Biomass Conference of the Americas: Energy, Environment, Agriculture, and Industry, 1995, pp. 901-910.
Wong, A., et al.; "Technical and Economic Aspects of Manufacturing Cetane-Enhanced Diesel Fuel from Canola Oil"; Bio-Oils Symposium; Saskatoon, Saskatchewan, Canada; Mar. 2-3, 1994.
Ali, et al., "Mineral Composition, Quality and Physico-chemical Parameters of the Local Tallow of Pakistan," Pakistan Journal of Nutrition, 7(5): 717-720, 2008.
American Petroleum Institute, Properties of Hydrocarbons of High Molecular Weight Synthesized by Research Project 42 of the American Petroleum Institute (1967).
ASTM International, Designation: D6751-11b, "Standard Specification for Biodiesel Fuel Blend Stock (B100) for Middle Distillate Fuels," Jul. 2011, pp. 1083-1091.
B.B. He and J. Van Gerpen "Biodiesel Quality Affected by Sulfur Content Originated by Different Feedstocks and a Database for the Same" Final Report KLK432 N08-04, National Institute for Advanced Transportation Technology, University of Idaho (Feb. 2008).
Bell, et al., "Biodiesel," Team Report for Imperial Oil, Queen's University, Kingston, Ontario, Apr. 2007. (106 pages).
CanmetENERGY's SuperCetane Technology, Natural Resources Canada, http://cetcyareness.nrcan.gc.ca/eng/industrialprocesses/industrialenergysystems, Nov. 2008, Accessed Jul. 19, 2013 (4 pages).
Connor, et al., "Hydrogenolysis of Oxygenated Organic Compounds," J. Am. Chem. Soc., 54(12), 1932, pp. 4678-4690.
Craig, et al., "A Marketing Survey of Worldwide Potential for Use of Vegetable Oil Conversion Products in Diesel Fuel," Saskatchewan Research Council, Oct. 1989 (182 pages).
Declaration of Jaques Monnier under 37 C.F.R. 1.132, dated Jan. 7, 2010, filed in U.S. Appl. No. 11/234,175.
Elliott, et al., "Hydrodeoxygenation of Wood-Derived Liquids to Produce Hydrocarbon Fuels," Proceedings of the 20th Intersociety Energy Conversion Engineering Conf., vol. 1 of 3, 1985. (9 pages).
File History of U.S. Appl. No. 08/269,090 to Monnier et al. (filed Jun. 30, 1994) (abandoned).
File History of U.S. Appl. No. 08/517,421 to Monnier et al. (filed Aug. 21, 1995) (continuation-in-part).
Food Fats and Oils, Inst. of Shortening and Edible Oils, 335-354 (9th Ed. 2006).
Ghosh, et al., "Detailed Composition-Based Model for Predicting the Cetane No. of Diesel Fuels," Ind. Eng. Chem. Res. 2006, 45, 346-351.
Goodfellow, J., "Animal Fat-Based Biodiesel: Explore Its Untapped Potential," Biodiesel Magazine, Feb. 10, 2009 (1 page).
Goodfellow, J., "Biofuel Production From Animal Fats: A North American Perspective," Sanimax Energy (23 pages).
Gorshteyn, et al., "ExxonMobil Catalytic Dewaxing—A Commercial Proven Technology," Paper presented at the 2nd Russian Refining Technology Conference, Moscow, Sep. 26-27 (2002), 13 pages.
Gosselink, et al., "Mild Hydrotracking: Coping with Catalyst Deactivation," 34 Catalyst Deactivation, 279-287 (1987).
Haas, M., "Animal Fats," Baileys Industrial Oil and Fat Products, 6th Ed., vol. 1: Edible Oil and Fat Products: Chemistry, Properties, and Health Effects, 2005, pp. 161-212.

(56) References Cited

OTHER PUBLICATIONS

Hammami, et al., "Cloud Points: Can We Measure or Model Them?" Petroleum Science and Technology, vol. 21, Nos. 3 & 4, 2003, pp. 345-358.

Held, et al., "Production of Hydrocarbons from Biomass," Energy from Biomass: 3rd E.C. Conference, International Conference on Biomass, Venice, 1985 (7 pages).

J. Johnson, et al. "Emissions from Fischer-Tropsch Diesel Fuels" SAE Technical Paper 2001-01-3518 (published Sep. 24, 2001).

Kubicka, et al., "Transformation of Plant Oils to Hydrocarbons," APROCHEM 2007, 1149-1155, Apr. 16-18, 2007.

L. Rantanen, R. Linnaila, P. Aakko, and T. Harju "NExBTL—Biodiesel Fuel of the Next Generation" SAE Technical Paper 2005-01-3771 (published Oct. 24, 2005).

L.G. Huve "Shell Global Solutions Dewaxing Technologies & Catalysts Current Status" pp. 1-13., 2007.

Latondress, E.G., "Refining, Bleaching and Hydrogenating Meat Fats," JAOCS, vol. 62, No. 4, 1985, pp. 812-815.

Laurent, et al., "Study of the hydrodeoxygenation of carbonyl, carboxylic and guaiacyl groups over sulfided CoMo/ $\gamma$-Al2O3 and NiMo/ $\gamma$-Al2O3 catalyst," App. Catal. A 109, pp. 97-115 (1994).

Leng, et al., "Catalytic Conversion of Palm Oil to Fuels and Chemicals," The Canadian Journal of Chemical Engineering, vol. 77, Feb. 1999, pp. 156-162.

Long, et al., "A Simple Test to Detect Chlorophyll in Tallow," Presented before the 8th Annual Fall Meeting - A.O.C.S., Oil & Soap, 1935. (2 pages).

Neste Oil, NExBTL Renewable Synthetic Diesel, Cal Hodge handout presented at Climate Action Team Technology Symposium, Sacramento, California, Jun. 27-28, 2006, available at http://www.climatechange.ca.gov/events/2006-06-27 28_symposium/presentations/ (last modified May 7, 2008).

Properties of Isononane—High Quality Chemical Properties, Accessed at http://chemeo.com/cid/73-453-8 on Aug. 23, 2013 (2 pages).

Sandler, S., "Chemical and Engineering Thermodynamics," at 1-3, 324-33, 598-603 (3rd Ed. 1999).

Santana, et al., "Evaluation of Different Reaction Strategies for the Improvement of Cetane Number in Diesel Fuels," Fuel 85: 643-656 (2006).

Satterfield, C.N., Heterogeneous Catalysis in Industrial Practice, 2nd Edition, Sections 9.8—9.11, McGraw-Hill, Inc., NY (1991), pp. 375-389.

Sixth Canadian Bioenergy R&D Seminar, Richmond, B.C., 1987 (19 pages).

Smith, et al., "Introduction to Chemical Engineering Thermodynamics," 5th Ed., 1996, pp. 526-531.

Song, et al., Temperature Programmed Retention Indices for Gc and Gc-Ms of Hydrocarbon Fuels and Simulated Distillation GC of Heavy Oils, Analytical Advances for Hydrocarbon Research, 147-210, 2003.

Standard Methods for the Analysis of Oils, Fats and Derivatives, 6th Ed., Part 1, pp. 96-108 (Pergamon Press 1979).

Stumborg, et al., "Catalytic Conversion of Vegetable Oils to Diesel Additives," Energy from Biomass and Wastes XVI, pp. 721-738, 1993.

Tempier, et al., "Identifying Environmentally Preferable Uses for Biomass Resources," Ch. 4, (Mar. 31, 2004).

Widmor, et al., "Prediction of the Freeze Point Temperature of Jet Fuel Using a Thermodynamic Model," Petroleum Chem. Div. Preprints, 47(3): 329-242 (2002).

Wong, A., Arbo-Tane, The Green Diesel Fuel, Naval Stores Review 14-15 (Jul./Aug. 1991).

Wong, et al., Bio-Based Cetane Enhancer for Diesel Fuels, BioEnergy 1998: Great Lakes Regional Biomass Energy Progarm. (12 pages).

Wong, Tall Oil-Based Cetane Enhancer for Diesel Fuel, in 79th Annual Meeting, Technical Section, Canadian Pulp and Paper Association, Preprints "A", A313-A318, held Jan. 26-27, 1993.

ASTM International, "Standard Specification for Fuel Oils", Designation: D396-09a, 2009, 7 pages.

ASTM International, "Standard Test Method for Determining Aerobic Aquatic Biodegradation of Lubricants or Their Components", Designation: D5864-05, 2005, 7 pages.

ASTM International, "Standard Test Method for Heat of Combustion of Liquid Hydrocarbon Fuels by Bomb Calorimeter (Precision Method)", Designation: D4809-09a, Apr. 2010, 10 pages.

ASTM International, "Standard Test Method for Oxidation Stability of Distillate Fuel Oil (Accelerated Method)", Designation: D2274-03a, 2008, 6 pages.

Chevron Phillips Chemical Co., "Material Safety Data Sheet; Diesel Cetane Check Fuel, High," Revised Apr. 17, 2013, 14 pages.

Chevron Phillips Chemical Co., "Material Safety Data Sheet; Diesel No. 2 Test Fuel," Revised Oct. 25, 2012, 14 pages.

Hess Corp., "Safety Data Sheet No. 9909; Diesel Fuel, All Types," Revised Aug. 30, 2012, 10 pages.

Hollebone, B., "Biofuels in the Environment; A Review of Behaviors, Fates and Effects & Remediation Techniques," Environment Canada Freshwater Spills Symposium, St. Louis, MO, 2009.

Irwin, R.J., et al. 1997. "Environmental Contaminants Encyclopedia," Alkanes Entry. National Park Service, Water Resources Division, Fort Collins, Colorado. (Distributed within the Federal Government as an Electronic Document).

Irwin, R.J., et al. 1997. "Environmental Contaminants Encyclopedia," Diesel Oil Entry. National Park Service, Water Resources Division, Fort Collins, Colorado. (Distributed within the Federal Government as an Electronic Document).

Irwin, R.J., et al. 1997. "Environmental Contaminants Encyclopedia," Mineral Spirits Entry. National Park Service, Water Resources Division, Fort Collins, Colorado. (Distributed within the Federal Government as an Electronic Document).

Khan, et al., "A Comparison of Acute Toxicity of Biodiesel, Biodiesel Blends, and Diesel on Aquatic Organisms," Journal of the Air & Waste Management Association, 2007, 53:3, 286-296.

OECD Guidance Document on Aquatic Toxicity Testing of Difficult Substances and Mixtures, No. 23, Sep. 2000, 53 pages.

OECD Guideline for Testing of Chemicals / Section 2: Effects on Biotic Systems, Test No. 202: Daphnia sp. Acute Immobilisation Test (Apr. 2004), 12 pages.

Sasol North America Inc., "Material Safety Data Sheet; LINPAR 1416-V Normal Paraffin," Revised Mar. 13, 2012, 8 pages.

U.S. Environmental Protection Agency: Research Triangle Park, NC, "Methods for Measuring Acute Toxicity of Effluents and Receiving Waters to Freshwater and Marine Organisms," 5th ed., Oct. 2002, 275 pages.

Akzo Nobel Catalyst Presentation, Oct. 2003 (63 pages).

Alencar, J.W., et al., Pyrolysis of Tropical Vegetable Oils, J. Agric. Food Chem., vol. 31, 1983, pp. 1268-1270.

Arca, M., et al., Evidence Contrary to the Accepted Diels-Alder Mechanism in the Thermal Modification of Vegetable Oils, J. Am. Oil Chem. Soc., 89 (2012), pp. 987-994.

Bradley, T.F., et al., Drying Oils and Resins, Ind. & Eng. Chem., vol. 32, No. 6, 1940, pp. 802-809.

Declaration of Jukka Myllyoja, Mar. 11, 2009, US Patent No. 8,022,258 File History (7 pages).

Duncan, D.P. In "Naval Stores," Zinkel, et al., Editors, Pulp Chemicals Association, New York, 1989, pp. 388-389.

Formo, M.W., Ester Reactions of Fatty Materials, J. Am. Oil Chem. Soc., vol. 31, 1954, pp. 548-559.

Gunstone, F.D., et al., "The Lipid Handbook," Ch. 3 & 6, Chapman & Hall, Second Edition, 1994.

Laurent, et al., "Study of the hydrodeoxygenation of carbonyl, carboxylic and guaiacyl groups over sulfided CoMo/ $\gamma$-Al2O3 and NiMo/ $\gamma$-Al2O3 catalyst," App. Catal. A 109, pp. 77-96 (1994).

Leonard, E.C., Polymerization—Dimer Acids, J. Am. Oil Chem. Soc., vol. 56, 1979, pp. 782A-785A.

Nawar, W.W., Thermal Degradation of Lipids. A Review, J. Agr. Food Chem, vol. 17, No. 1, 1969, pp. 18-21.

Neste's Mar. 17, 2008 response to an Office Action, US Pat. No. 8,022,258 File History (13 pages).

Neste's Oct. 19, 2009 response to an Office Action, US Pat. No. 8,022,258 File History (9 pages).

(56) References Cited

OTHER PUBLICATIONS

Paschke, R.F. et al., Dimer Acid Structures. The Thermal Dimer of Methyl 10-trans, 12-trans, Linoleate, J. Am. Oil Chem. Soc., vol. 41, 1964, pp. 723-727.

Paschke, R.F., et al., Thermal Polymerization of Unsaturated Fatty Esters Normal Methyl Linoleate, J. Am. Oil Chem. Soc., 1949, pp. 278-283.

Petrocelli, F.P. et al., Modeling Lignin Liquefaction—Catalytic Hydroprocessing of Lignin-Related Methoxyphenols and Interaromatic Unit Linkages, Fuel Sci. & Tech., 5(1), 1987, pp. 25-62.

Senol, et al., Hydrodeoxygenation of aliphatic esters on sulphided NiMo/ $\gamma$-Al2O3 and CoMo/ $\gamma$-Al2O3 catalyst: The effect of water, Catalysis Today, 106 (2005), pp. 186-189.

Senol, et al., Hydrodeoxygenation of methyl esters on sulphided NiMo/ $\gamma$-Al2O3 and CoMo/ $\gamma$-Al2O3 catalysts, Catalysis Today, 100 (2005), pp. 331-335.

Sharp, D.W.A., The Penguin Dictionary of Chemistry, Second Edition, 1990, pp. 207, 263, 432, 433.

Venkatachalam, et al., Kinetics of Oligomerization of Methyl Ester of Dehydrated Castor Oil Fatty Acid over Molybdenum Oxide on Silica-Alumina Catalyst in Comparison with the Thermal Oligomerization Process, J. Poly. Sci. Poly. Chem. Ed., vol. 22, 1984, pp. 3805-3814.

Second Declaration of Edward Sughrue dated Jan. 13, 2014 (63 pages).

Second Declaration of Nelson E. Lawson dated Jan. 12, 2014 (9 pages).

Petitioner's Opposition to Patent Owner's Motion to Amend, filed in the Inter Partes Review of US Patent No. 8,212,094 (IPR2013-00178) on Jan. 13, 2014 (22 pages).

Affens, et al., "Effect of Composition on Freezing Points of Model Hydrocarbon Fuels," presented before the Division of Fuel Chemistry, American Chemical Society, New York, Aug. 1981, 9 pages, available at https://web.anl.gov/PCS/acsfuel/preprint%20archive/Files/26_3_NEW%20YORK_08-81_0178.pdf (subsequently published in Fuel, 63(4), Apr. 1984, pp. 543-547).

B. Lee, et al., "Bioremediation and Ecotoxicity of Drilling Fluids Used for Land-based Drilling," AADE Technical Conference, Houston, Apr. 2002, pp. 1-12.

Beare-Rogers, J. et al, "Lexicon of Lipid Nutrition," Pure and Applied Chemistry, vol. 73, No. 4, 2001, pp. 685-744.

Chaurasia, et al., "Quantitation of Fatty Acids and Hydroxy Fatty Acids by Gas Chromatography/Mass Spectrometry. Predictively Useful Correlations of Relative Response Factors with Empirical Formula," Journal of Mass Spectrometry, 30:1018-1022 (1995).

Chevron Philips Chemical Co., "Synfluid PAO 2 cSt Material Safety Data Sheet," revised Aug. 2005, accessed at http://www.leco.com/component/edocman/?task=document.viewdoc&id=592, 8 pages.

Communication dated May 26, 2014 from the Technische Informationsbibliothek and Universitätsbibliothek Hannover, Germany (English translation included—3 pages).

D.V. Hale, et al, "Phase Change Materials Handbook," NASA Contractor Report 61363, Sep. 1971, 204 pages.

European Committee for Standardization (CEN), "Automotive fuels—Paraffinic diesel from synthesis or hydrotreatment—Requirements and test methods," TC WI WS038: 2009 (E), 10 pages.

European Food Safety Authority, "Scientific Opinion on the re-evaluation of candelilla wax (E 902) as a food additive," EFSA Journal 2012;10(11): 2946 (published Jan. 28, 2013), 27 pages.

European Standard EN 590:2004, "Automotive Fuels—Diesel—Requirements and Test Methods," Swedish Standards Institute, 2004, English version, available at http://www.repsol.com/imagenes/es_gl/EN%20590_04_93548_tcm10-67163.pdf, 13 pages.

ExxonMobil Chemical, "Product Safety Summary—ISOPARTM M Fluid," 2011, 3 pages.

ExxonMobil, "Material Safety Data Sheet—ISOPAR M Fluid," 2002 (Revised 2007, 2008), 10 pages.

Filter Manufacturers Council, "Solving Winter Diesel Fuel / Fuel Filter Problems," Technical Service Bulletin 91-1R3, 1991 (Revised 2006), available at http://www.hastingsfilter.com/Literature/TSB/91-1R3.pdf, 2 pages.

Göröcs, et al., "The Determination of GC013MS Relative Molar Responses of Some n-Alkanes and their Halogenated Analogs," Journal of Chromatographic Science, 51:138-145 (2013).

Griesbaum, et al., "Hydrocarbons," Ullmann's Encyclopedia of Industrial Chemistry, 2000, 61 pages.

Iki, et al., "Vegetable Oil Hydrogenating Process for Automotive Fuel," SAE Technical Paper, Jul. 23, 2007, pp. 1871-1876.

Kirk-Othmer, "Concise Encyclopedia of Chemical Technology," John Wiley & Sons, Inc., New York NY, pp. 367-369, (1985).

Lange, N.A., "Lange's Handbook of Chemistry," (Ed. Dean, J.A.), Thirteenth Edition, 1985, pp. 7.375 & 7.626.

Rantanen, et al., "NExBTL—Biodiesel Fuel of the Second Generation," SAE Technical Paper 2005-01-3771 (published Oct. 24, 2005), 17 pages.

Sinha, et al., "Hydroisomerization of n-Alkanes over Pt-SAPO-11 and Pt-SAPO-31 Synthesized from Aqueous and Nonaqueous Media," Ind. Eng. Chem. Res., 1998, 37 (6), pp. 2208-2214.

TCI America, "Material Safety Data Sheet—5-Methylnonane," 2010, 3 pages.

Tong, et al., "Flame Ionization Detector Response Factors for Compound Classes in Quantitative Analysis of Complex Organic Mixtures," Anal. Chem., 56:2124-2128 (1984).

Wong, et al., Bio-Based Cetane Enhancer for Diesel Fuels, BioEnergy 1998: Great Lakes Regional Biomass Energy Program. (12 pages).

\* cited by examiner

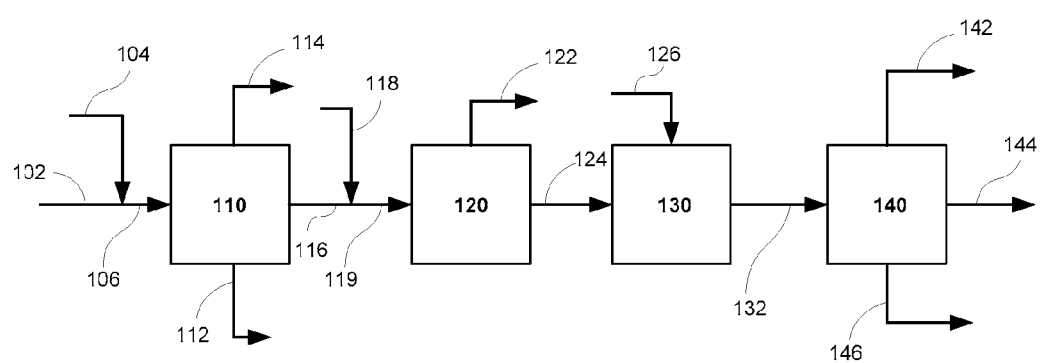

BIO-BASED SYNTHETIC FLUIDS

CROSS-REFERENCE TO RELATED APPLICATIONS

This application claims the benefit of priority from U.S. Provisional Application No. 61/809,183, filed on Apr. 5, 2013, which is incorporated herein by reference in its entirety for any and all purposes.

FIELD

The technology relates to production of synthetic fluids from bio-derived feeds. More particularly, this technology relates to methods for conversion of animal fat, vegetable oils, and other sources of bio-based fatty acid/esters into paraffinic fluids suitable for use as solvents, industrial process fluids, and lubricating base oils.

BACKGROUND

Low aromatic hydrocarbon fluids, i.e. typically containing less than 1 wt % total aromatics, are used in a diverse range of applications where chemical inertness, thermal/oxidative stability, low toxicity, and low odor are desired. These hydrocarbons are characterized by their paraffinic nature, a carbon number distribution in the $C_5$-$C_{40}$ range, preferably in the $C_{15}$-$C_{40}$ range. For most applications, the preferred fluids have a flash point greater than about 100° C. Other properties specified for hydrocarbon fluids include viscosity (specification range dictated by application), and pour point (typically <−10° C.). Mineral oil is an example of a low aromatic hydrocarbon fluid.

As a result of a number of industry trends, such as increased demand for drilling and hydraulic fracturing fluids and tightening environmental standards concerning eco-toxicity, biodegradability, and work place safety/health, demand for such paraffinic fluids has experienced rapid growth. This has coincided with an increased demand for middle distillate fuels ($C_{10}$-$C_{20}$ hydrocarbons) that compete for much of the same petroleum molecules. Furthermore, with high aromatic feeds such as tar sands finding their way into the North American petroleum pool, more extensive upgrading (such as aromatic hydrogenation) is required in order to meet fluid product specifications. Use of mineral oils in cosmetics and food preparation is banned in the European Union due to concerns about presence of trace amounts of carcinogenic polyaromatic hydrocarbons—thus providing the need for synthetic products that are inherently free of these aromatic components.

Synthetic hydrocarbon products have been used for some industrial fluid applications. For example $C_{16}$/$C_{18}$ linear alpha olefins (LAOS) from oligomerization of ethylene, are used as drilling base fluids. However, this synthetic route is non-selective, producing a wide distribution of even carbon number LAOS, mostly in the $C_4$ to $C_{10}$ range, such that further expensive processing and separation steps are required to achieve the desired LAO product. Moreover, these even carbon number LAOs in the $C_4$ to $C_{10}$ range are chemical intermediates and not end-products suitable for use in industrial fluid applications.

Use of the Fischer-Tropsch process for producing synthetic hydrocarbons suitable for certain hydrocarbon fluid applications has also been reported. However, the FT process is very capital intensive and most of the FT manufacturing is dedicated to fuel production. Because the hydrocarbon range of interest for synthetic hydrocarbon fluids comprises a small percentage of the wide distribution of FT hydrocarbons (C1-C50+), it is more economical to hydrocrack and hydrotreat the FT wax and light oil fractions into complex compositions for fuel use.

There is thus a need for new processes for producing hydrocarbon fluids from alternative feeds. More specifically, there is a need for hydrocarbon fluid products that, based on their feedstocks and conversion processes, are substantially free of aromatics without further processing such as by aromatic hydrogenation conditions.

SUMMARY

In an aspect, a method is provided involving altering the viscosity of bio-derived paraffins to produce a paraffinic fluid, where the altering step includes oligomerizing bio-derived paraffins, unsaturating bio-derived paraffins, chlorinating bio-derived paraffins, or a combination of any two or more thereof; the bio-derived paraffins are produced by hydrodeoxygenating a bio-based feed; the bio-based feed comprises bio-derived fatty acids, fatty acid esters, or a combination thereof; the bio-derived paraffins comprise n-paraffins; and the n-paraffins have a kinematic viscosity of less than about 10 cSt at 40° C. and have a biodegradability of at least 40% after about 23 days of exposure to microorganisms.

In some embodiments, oligomerizing bio-derived paraffins includes contacting the bio-derived paraffins with an organic peroxide to produce an oligomerized product, where the oligomerized product has a kinematic viscosity of at least about 10 cSt at 40° C. In some embodiments, the oligomerized product has a biodegradability of at least about 40% after about 23 days of exposure to microorganisms. In some embodiments, the oligomerized product is a dimer, trimer, tetramer, or a mixture of any two or more thereof. In some embodiments, the organic peroxide is present in an amount between about 2 wt % and about 40 wt % based on the total weight of paraffins and organic peroxide. In some embodiments, the organic peroxide comprises di-tert butyl peroxide (DTBP), 2,5-dimethyl 2,5-di(t-butylperoxy)hexane, dicumyl peroxide, dibenzoyl peroxide, dipropyl peroxide, ethyl propyl peroxide, or tert-butyl tert-amyl peroxide. In some embodiments, the contacting is performed at a temperature between about 50° C. and about 250° C. In some embodiments, the oligomerized product is used as a drilling fluid, a hydraulic fracturing fluid, a metal working fluid, a protecting agent, or a combination of any two or more thereof.

In some embodiments, chlorinating the bio-derived paraffins includes contacting the bio-derived paraffins with chlorine gas at a temperature between about 60° C. and about 150° C. to produce a chlorinated product, where the chlorinated product comprises haloalkanes; and the chlorinated product has a kinematic viscosity of greater than about 10 cSt at 40° C. In some embodiments, the chlorinated product is used as a protecting agent, a cleaning agent, or a combination of both. In some embodiments, the chlorinated product acts as a flame retardant. In some embodiments, the chlorinated product is used to clean fabric, metal, or plastic.

In some embodiments, unsaturating the bio-derived paraffins comprises dehydrogenation of the bio-derived paraffins by contacting the bio-derived paraffins with a dehydrogenation catalyst at a temperature from about 360° C. to about 660° C. to produce an olefinic fluid, where the olefinic fluid comprises at least about 10 wt % internal olefins in the $C_{15}$ to $C_{18}$ range; and the olefinic fluids have a kinematic viscosity of less than about 10 cSt at 40° C. In some embodiments, the olefinic fluid comprises at least about 20 wt % internal olefins in the $C_{15}$ to $C_{18}$ range. In some embodiments, the method further involves oligomerizing the olefinic fluid to produce dimers, trimers, tetramers, or a mixture of any two or more thereof. In some embodiments, the olefinic fluid is used as a hydraulic fracturing fluid, as a drilling fluid, or a combination of the two.

In some embodiments, the bio-derived paraffins are produced by hydrodeoxygenating the bio-based feed to produce a hydrodeoxygenated product; and at least partially hydroisomerizing the hydrodeoxygenated product to produce a hydroisomerized product; where the bio-derived paraffins comprise the hydrodeoxygenated product and the hydroisomerized product; the hydrodeoxygenated product comprises n-paraffins; the hydroisomerized product comprises isoparaffins where at least about 80 wt % of the isoparaffins are mono-methyl branched paraffins; the mono-methyl branched paraffins comprise less than about 30 wt % terminal branched isoparaffins; and the isoparaffins have a kinematic viscosity of less than about 10 cSt at 40° C. and have a biodegradability of at least about 40% after about 23 days of exposure to microorganisms. In some embodiments, the hydrodeoxygenated product includes n-paraffins in the range of about 80 wt % to about 100 wt %; cycloparaffins in the range of about 1 wt % to about 10 wt %; and less than about 1 wt % total aromatics.

In some embodiments, the bio-derived fatty acids, fatty acid esters, or a combination thereof comprises algae oils, beef tallow, camelina oil, canola oil, rapeseed oil, castor oil, choice white grease, coconut oil, coffee bean oil, corn oil, cottonseed oil, fish oils, hemp oil, Jatropha oil, linseed oil, mustard oil, palm oil, palm kernel oil, poultry fat, soybean oil, sunflower oil, tall oil, tall oil fatty acid, Tung oil, used cooking oils, yellow grease, products of the food industry, or combinations of any two or more thereof. In some embodiments, the bio-derived fatty acids, fatty acid esters, or a combination thereof comprise soybean oil, corn oil, cottonseed oil, canola oil, coconut oil, sunflower oil, palm oil, palm kernel oil, rapeseed oil, or a combination of any two or more thereof.

In an aspect, a method is provided involving producing an orifice in a substrate by at least injecting a viscosity-altered paraffinic fluid into the substrate, wherein the paraffinic fluid includes a hydrodeoxygenated product and a hydroisomerized product; the hydrodeoxygenated product is produced by hydrodeoxygenating a bio-derived feed; the hydroisomerized product is produced by at least partially hydroisomerizing the hydrodeoxygenated product; the bio-derived feed includes bio-derived fatty acids, fatty acid esters, or a combination thereof; the hydrodeoxygenated product includes n-paraffins; the hydroisomerized product includes isoparaffins; the paraffinic fluid contains less than about 1 wt % aromatics; and the n-paraffins have a kinematic viscosity of less than about 10 cSt at 40° C. and have a biodegradability of at least about 40% after about 23 days of exposure to microorganisms; the isoparaffins are at least about 80 wt % mono-methyl branched paraffins where the mono-methyl branched paraffins comprise less than about 30 wt % terminal branched isoparaffins, have a kinematic viscosity of less than about 10 cSt at 40° C., and have a biodegradability of at least about 40% after about 23 days of exposure to microorganisms. In some embodiments, the substrate includes a soil substrate, a topsoil substrate, a subsoil substrate, a clay substrate, a sand substrate, a rock substrate, or a stone substrate. In some embodiments, the step of producing an orifice includes hydraulic fracturing of the substrate with the paraffinic fluid.

In another aspect, a method is provided involving protecting a substance by applying a paraffinic fluid. In the method, the paraffinic fluid includes a hydrodeoxygenated product; where the hydrodeoxygenated product is produced by hydrodeoxygenating a bio-derived feed; the bio-derived feed comprises bio-derived fatty acids, fatty acid esters, or a combination thereof; the hydrodeoxygenated product comprises n-paraffins; the paraffinic fluid contains less than 1 wt % aromatics; and the n-paraffins have a kinematic viscosity of less than about 10 cSt at 40° C. and have a biodegradability of at least 40% after about 23 days of exposure to microorganisms. In some embodiments, the hydrodeoxygenated product includes n-paraffins in the range of about 80 wt % to about 100 wt %; cycloparaffins in the range of about 1 wt % to about 10 wt %; less than about 1 wt % total aromatics. In some embodiments, the paraffinic fluid further comprises a hydroisomerized product produced by at least partially hydroisomerizing the hydrodeoxygenated product; where the hydroisomerized product comprises isoparaffins where at least about 80 wt % of the isoparaffins are mono-methyl branched paraffins; the mono-methyl branched paraffins comprise less than about 30 wt % terminal branched isoparaffins; and the isoparaffins have a kinematic viscosity of less than about 10 cSt at 40° C. and have a biodegradability of at least about 40% after about 23 days of exposure to microorganisms.

In some embodiments, the substance is a food crop, a metal, or wood. In some embodiments, protecting involves solvating the substance. In such embodiments, the substance includes pesticides, herbicides, paints, inks, or coatings. In some embodiments, protecting involves cleaning the substance with the paraffinic fluid In such embodiments, the substance comprises fabric, metal, or plastic. In some embodiments, protecting involves lubricating the substance where the substance is metal.

In an aspect, a method is provided which involves producing an orifice in a substrate by at least injecting a paraffinic fluid into the substrate, wherein the paraffinic fluid comprises a hydrodeoxygenated product; the hydrodeoxygenated product is produced by hydrodeoxygenating a bio-derived feed; the bio-derived feed comprising bio-derived fatty acids, fatty acid esters, or a combination thereof; the hydrodeoxygenated product comprises n-paraffins; the paraffinic fluid contains less than about 1 wt % aromatics; and the n-paraffins have a kinematic viscosity of less than about 10 cSt at 40° C. and have a biodegradability of at least about 40% after about 23 days of exposure to microorganisms. In some embodiments, the hydrodeoxygenated product includes n-paraffins in the range of about 80 wt % to about 100 wt %; cycloparaffins in the range of about 1 wt % to about 10 wt %; and less than about 1 wt % total aromatics. In some embodiments, the paraffinic fluid further includes a hydroisomerized product produced by at least partially hydroisomerizing the hydrodeoxygenated product; wherein the hydroisomerized product comprises isoparaffins where at least about 80 wt % of the isoparaffins are mono-methyl branched paraffins; the mono-methyl branched paraffins comprise less than about 30 wt % terminal branched isoparaffins; and the isoparaffins have a kinematic viscosity of less than about 10 cSt at 40° C. and have a biodegradability of at least about 40% after about 23 days of exposure to microorganisms.

In some embodiments, the substrate comprises a soil substrate, a topsoil substrate, a subsoil substrate, a clay substrate, a sand substrate, a rock substrate, or a stone substrate. In some embodiments, the bio-derived fatty acids, fatty acid esters, or a combination thereof comprises algae oils, beef tallow, camelina oil, canola oil, rapeseed oil, castor oil, choice white grease, coconut oil, coffee bean oil, corn oil, cottonseed oil, fish oils, hemp oil, Jatropha oil, linseed oil, mustard oil, palm oil, palm kernel oil, poultry fat, soybean oil, sunflower oil, tall oil, tall oil fatty acid, Tung oil, used cooking oils, yellow grease, products of the food industry, or combinations of any two or more thereof. In some embodiments, the bio-derived fatty acids, fatty acid esters, or a combination thereof comprise soybean oil, corn oil, cottonseed oil, canola oil, coconut oil, sunflower oil, palm oil, palm kernel oil, rapeseed oil, or a combination of any two or more thereof. In some embodiments, the step of producing an orifice comprises hydraulic fracturing of the substrate with the paraffinic fluid.

BRIEF DESCRIPTION OF THE DRAWING

FIG. 1 depicts a process for conversion of a bio-derived feed to industrial fluids, the process comprising hydrodeoxygenation, hydroisomerization, peroxide-initiated oligomerization, and fractionation

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl or aryl group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkylperoxy, alkenoxy, alkynoxy, aryloxy, arylperoxy, aralkyloxy; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano (i.e. CN), alkoxy, and/or halo groups such as F, Cl, Br, and I groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

As used herein, "aryl" groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

The term "microorganisms" as used herein refers to microbes capable of degrading hydrocarbons.

The term "paraffins" as used herein means branched or unbranched hydrocarbon alkanes. An unbranched paraffin is an n-paraffin; a branched paraffin is an isoparaffin.

The term "paraffinic" as used herein means both paraffins as defined above as well as predominantly hydrocarbon chains possessing regions that are alkane, either branched or unbranched, with mono- or di-unsaturation (i.e. one or two double bonds), halogenation from about 30 wt % to about 70 wt %, or where the hydrocarbon is both unsaturated and halogenated. However, the term does not describe a halogen on a carbon involved in a double bond.

The phrase "$C_2+$ chain branching" as used herein means alkyl branches wherein the alkyl group has two or more carbons; e.g. ethyl or isopropyl branches.

"Protecting" as used herein includes, but is not limited to, solvating, coating, cleaning, lubricating, or preserving a substance, surface, or composition.

"Orifice" as used herein encompasses holes, channels, fractures, and fissure; in other words, the term encompasses spaces of any three-dimensional length, width, and diameter that are not filled with solid material.

The present technology provides bio-based synthetic fluids as well as methods for making the fluids and methods that utilize the advantageous properties of the bio-based synthetic fluids, as discussed herein.

In an aspect, a method is provided involving altering the viscosity of bio-derived paraffins to produce a paraffinic fluid, where the altering step includes oligomerizing bio-derived paraffins, unsaturating bio-derived paraffins, chlorinating bio-derived paraffins, or a combination of any two or more thereof; the bio-derived paraffins are produced by hydrodeoxygenating a bio-based feed; the bio-based feed comprises bio-derived fatty acids, fatty acid esters, or a combination thereof; the bio-derived paraffins comprise n-paraffins; and the n-paraffins have a biodegradability of at least about 40% after about 23 days of exposure to microorganisms. The biodegradability may be about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, and ranges between any two of these values or greater than any one of these values. In some embodiments, the paraffinic fluid contains below about 1 wt % total aromatics. The paraffinic fluid may contain aromatics in the amount of about 0.9 wt %, about 0.8 wt %, about 0.7 wt %, about 0.6 wt %, about 0.5 wt %, about 0.4 wt %, about 0.3 wt %, about 0.2 wt %, about 0.1 wt %, and ranges between any two of these values or below any one of these values. In some embodiments, the paraffinic fluid contain less than 0.1 wt % total aromatics. In some embodiments, the paraffinic fluid is free of benzene.

In some embodiments, the paraffinic fluid has a kinematic viscosity less than about 10 cSt at 40° C. In such embodiments, the paraffinic fluid may have a kinematic viscosity at 40° C. of about 9 cSt, about 8 cSt, about 7 cSt, about 6 cSt, about 5 cSt, about 4 cSt, about 3 cSt, about 2 cSt, about 1 cSt, and ranges in between any two of these values or below any one of these values. In some embodiments, the paraffinic fluid has a kinematic viscosity greater than about 10 cSt at 40° C. In such embodiments, the paraffinic fluid may have a kinematic viscosity at 40° C. of about 12 cSt, about 14 cSt, about 16 cSt, about 18 cSt, about 20 cSt, about 22 cSt, about 24 cSt, about 26 cSt, about 28 cSt, about 30 cSt, and ranges in between any two of these values or greater than any one of these values. In some embodiments, the paraffinic fluid has a kinematic viscosity greater than about 20 cSt at 40° C.

Bio-Based Feed: Bio-derived fatty acids, fatty acid esters, or combinations thereof, are utilized as the bio-based feed for making the fluids described throughout this application. The bio-derived fatty acids, fatty acid esters, or combinations thereof include algae oils, beef tallow, camelina oil, canola/rapeseed oil, castor oil, choice white grease, coconut oil, coffee bean oil, corn oil, fish oils, hemp oil, Jatropha oil, linseed oil, mustard oil, palm oil, poultry fat, soybean oil, sunflower oil, tall oil, tall oil fatty acid, Tung oil, used cooking oils, yellow grease, products of the food industry, or combinations of any two or more thereof. In some embodiments, the bio-derived fatty acids, fatty acid esters, or combinations thereof include soybean oil, corn oil, cottonseed oil, canola oil, coconut oil, sunflower oil, palm oil, palm kernel oil, rapeseed oil, or a combination of any two or more thereof.

In their natural form, most of these fats and oils contain phosphorus as well as metals such as calcium, magnesium, sodium, potassium, iron, and copper. Additionally, most also contain nitrogen compounds such as chlorophyll or amino acids. When the level of phosphorus is greater than about 40 wppm, and total metals greater than about 30 wppm, the fats and oils may be subjected to treatment steps including, but not limited to, acid degumming, neutralization, bleaching, or a combination of any two or more thereof. Acid degumming involves contacting the fat/oil with concentrated aqueous acids. Exemplary acids are phosphoric, citric, and maleic acids. This pretreatment step removes metals such as calcium and magnesium in addition to phosphorus. Neutralization is typically performed by adding a caustic (referring to any base, such as aqueous NaOH) to the acid-degummed fat/oil. The process equipment used for acid degumming and neutralization includes high shear mixers and disk stack centrifuges.

Bleaching typically involves contacting the degummed fat/oil with adsorbent clay and filtering the spent clay through a pressure leaf filter. Use of synthetic silica instead of clay is reported to provide improved adsorption. The bleaching step removes chlorophyll and much of the residual metals and phosphorus. Any soaps that may have been formed during the caustic neutralization step (i.e. by reaction with free fatty acids) are also removed during the bleaching step. The aforementioned treatment processes are known in the art and described in the patent literature, including but not limited to U.S. Pat. Nos. 4,049,686, 4,698,185, 4,734,226, and 5,239,096. It should be recognized by those skilled in the art that other fat/oil treatment methods, including those involving alternate physical, thermal, and chemical processes, may be adapted to pretreatment of a bio-based feed.

Hydrodeoxygenation: The bio-based feed is subjected to hydrodeoxygenation (HDO) in a catalytic reactor wherein the fatty acids and/or fatty acid esters are converted to straight-chain paraffins. In hydrodeoxygenation, the oxygen atoms of the fatty acid/ester are removed through hydrogenolysis to form water, while the unsaturated carbon-carbon double bonds of the fatty acid chains are simultaneously hydrogenated. HDO may be accompanied by decarbonylation and decarboxylation reactions (wherein the oxygen atom is removed as CO and $CO_2$ respectively). The HDO reaction takes place at temperatures from about 200° C. to about 400° C., and hydrogen partial pressure between about 20 bar to about 160 bar. The HDO reaction may occur at a temperature of about 220° C., 240° C., 260° C., 280° C., 300° C., 320° C., 340° C., 360° C., 380° C., and ranges between any two of these values or above any one of these values. In some embodiments, temperature range is from about 260° C. to about 370° C. The HDO reaction may occur at a hydrogen partial pressure of about 30 bar, 40 bar, 50 bar, 60 bar, 70 bar, 80 bar, 90 bar, 100 bar, 110 bar, 120 bar, 130 bar, 140 bar, 150 bar, and ranges between any two of these values or above any one of these values. In some embodiments, the pressure range is from about 30 bar to about 130 bar. Suitable catalysts for the HDO process include sulfided forms of hydrogenation metals from Group VIB and Group VIII of the periodic table. Examples of suitable mono-metallic, bi-metallic, and tri-metallic catalysts include Mo, Ni, Co, W, CoMo, NiMo, NiW, NiCoMo. These catalysts may be supported on alumina, or alumina modified with oxides of silicon and/or phosphorus. These catalysts may be purchased in the reduced sulfide form, or more commonly purchased as metal oxides and sulfided during startup. To ensure these catalysts remain in the reduced sulfide form required for desired activity/selectivity balance, use of a "sulfur spike" compound such as dimethyl disulfide may be utilized. Fixed-bed and/or slurry reactor systems and operating conditions may be used. In some embodiments, continuous reactor systems are used. In some embodiments, continuous fixed-bed reactors are used. In continuous fixed-bed reactor systems, the liquid hourly space velocity (LHSV) is between about 0.2 $h^{-1}$ and about 10 $h^{-1}$, and the hydrogen gas-to-oil ratio (GOR at standard conditions) is between about 200 NL/L and about 1600 NL/L. The LHSV may be about 0.3 $h^{-1}$, about 0.4 $h^{-1}$, about 0.5 $h^{-1}$, about 0.6 $h^{-1}$, about 0.7 $h^{-1}$, about 0.8 $h^{-1}$, about 0.9 $h^{-1}$, about 1.0 $h^{-1}$, about 1.2 $h^{-1}$, about 1.4 $h^{-1}$, about 1.6 $h^{-1}$, about 1.8 $h^{-1}$, about 2.0 $h^{-1}$, about 2.2 $h^{-1}$, about 2.4 $h^{-1}$, about 2.6 $h^{-1}$, about 2.8 $h^{-1}$, about 3.0 $h^{-1}$, about 3.0 $h^{-1}$, about 3.2 $h^{-1}$, about 3.4 $h^{-1}$, about 3.6 $h^{-1}$, about 3.8 $h^{-1}$, about 4.0 $h^{-1}$, about 4.2 $h^{-1}$, about 4.4 $h^{-1}$, about 4.6 $h^{-1}$, about 4.8 $h^{-1}$, about 5.0 $h^{-1}$, about 5.2 $h^{-1}$, about 5.4 $h^{-1}$, about 5.6 $h^{-1}$, about 5.8 $h^{-1}$, about 6.0 $h^{-1}$, about 6.2 $h^{-1}$, about 6.4 $h^{-1}$, about 6.6 $h^{-1}$, about 6.8 $h^{-1}$, about 7.0 $h^{-1}$, about 7.2 $h^{-1}$, about 7.4 $h^{-1}$, about 7.6 $h^{-1}$, about 7.8 $h^{-1}$, about 8.0 $h^{-1}$, about 8.2 $h^{-1}$, about 8.4 $h^{-1}$, about 8.6 $h^{-1}$, about 8.8 $h^{-1}$, about 9.0 $h^{-1}$, about 9.2 $h^{-1}$, about 9.4 $h^{-1}$, about 9.6 $h^{-1}$, about 9.8 $h^{-1}$, and ranges between any two of these values or above any one of these values. In some embodiments with continuous fixed-bed reactor systems, the LHSV is from about 0.5 $h^{-1}$ to about 5.0 $h^{-1}$. The GOR may be about 250 NL/L, 300 NL/L, 350 NL/L, 400 NL/L, 450 NL/L, 500 NL/L, 550 NL/L, 600 NL/L, 650 NL/L, 700 NL/L, 750 NL/L, 800 NL/L, 850 NL/L, 900 NL/L, 950 NL/L, 1000 NL/L, 1050 NL/L, 1100 NL/L, 1150 NL/L, 1200 NL/L, 1250 NL/L, 1300 NL/L, 1350 NL/L, 1400 NL/L, 1450 NL/L, 1500 NL/L, 1550 NL/L, and ranges between any two of these values or above any one of these values. In some embodiments with continuous fixed-bed reactor systems, GOR is from about 400 NL/L to about 1400 NL/L.

The reactor effluent is directed to a high pressure separator for separating the gas stream containing unreacted hydrogen and gas phase byproducts such as water, CO, $CO_2$, $H_2S$, $NH_3$, and propane from the liquid HDO products. The gas is then cooled and directed to a three-phase cold separator drum. There a water stream with dissolved carbonate, bisulfide, and ammonium salts, a hydrocarbon stream containing light hydrocarbons, and a hydrogen rich gas stream are separated. The hydrogen rich gas is optionally scrubbed to remove the gas phase byproducts and recycled to the reactor. The liquid HDO product from the high pressure separator may also be partially recycled to the reactor to dilute the reactive bio-based feed to the exothermic HDO reactor.

Those skilled in the art recognize that variations to these operating conditions may be made based on purity of available hydrogen gas and to ensure proper three-phase ($H_2$ gas/liquid feed/solid catalyst) contacting regime within the reactor. The liquid paraffin product composition obtained from subjecting most fatty acid/ester bio-based feeds to HDO is a hydrocarbon composition rich in n-paraffins in the $C_{11}$ to $C_{22}$ range. The HDO product contains between about 80 wt % and 100 wt % n-paraffins, between about 0 wt % and about 20 wt % isoparaffins, between about 0 wt % and about 10 wt % cycloparaffins (also called naphthenes or naphthenics), between about 0 wt % and about 10% wt % olefins, and below about 1 wt % total aromatics. It is important to note that the method does not involve more severe aromatic hydrogenation conditions. The HDO product may contain n-paraffins in the amount of about 82 wt %, about 84 wt %, about 86 wt %, about 88 wt %, about 90 wt %, about 92 wt %, about 94 wt %, about 96 wt %, about 98 wt %, and ranges between any two of these values or above any one of these values. The n-paraffins have a biodegradability of at least about 40% after about 23 days of exposure to microorganisms. The biodegradability may be about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, and ranges between any two of these values or greater than any one of these values. The n-paraffins have a kinematic viscosity of less than about 10 cSt at 40° C. The n-paraffins may have a kinematic viscosity at 40° C. of about 9 cSt, about 8 cSt, about 7 cSt, about 6 cSt, about 5 cSt, about 4 cSt, about 3 cSt, about 2 cSt, about 1 cSt, and ranges in between any two of these values or below any one of these values.

The HDO product may contain cycloparaffins in the amount of about 1 wt %, about 2 wt %, about 3 wt %, about 4 wt %, about 5 wt %, about 6 wt %, about 7 wt %, about 8 wt %, about 9 wt %, and ranges between any two of these values or below any one of these values. The HDO product may contain aromatics in the amount of about 0.9 wt %, about 0.8 wt %, about 0.7 wt %, about 0.6 wt %, about 0.5 wt %, about 0.4 wt %, about 0.3 wt %, about 0.2 wt %, about 0.1 wt %, and ranges between any two of these values or below any one of these values. In some embodiments, the HDO product contains less than 0.1 wt % total aromatics. In some embodiments, the HDO product is free of benzene. The HDO product has a kinematic viscosity of less than about 10 cSt at 40° C. The HDO product may have a kinematic viscosity at 40° C. of about 9 cSt, about 8 cSt, about 7 cSt, about 6 cSt, about 5 cSt, about 4 cSt, about 3 cSt, about 2 cSt, about 1 cSt, and ranges in between any two of these values or below any one of these values.

The HDO product may be distilled to yield a synthetic renewable drilling base fluid in the $C_{16}$-$C_{18}$ range. This fluid has a flash point greater than about 100° C., a kinematic viscosity in the range of about 3 cSt to about 4 cSt at 40° C., a pour point of about 16° C. to about 20° C., high thermal and oxidative stability due to paraffinic structure (i.e. having a total insoluble content of 0.2 mg/100 mL or less according to the ASTM D2274 accelerated oxidative aging method when 20 wppm or more anti-oxidant is added to the fluid), low aquatic toxicity and ecotoxicity (i.e. having an $LC_{50}$ value of 3.5 mg/L or higher where $LC_{50}$ is the concentration at which half a population of the organism dies of ingesting the fluid, and is typically the average of 24 hour, 48 hour, and 72 hour exposure tests on *Daphia magna, Pimephales promelas*, or Rainbow Trout), and a biodegradability greater than about 40% according to ASTM D5864-05, incorporated herein by reference. ASTM D5864-05 measures how much of a material breaks down into $CO_2$ by microorganisms over a period of 23 days. In contrast to the paraffins of this application, typical petroleum-based mineral oils have biodegradability in the 15-35% range, while synthetic oils like poly alpha-olefins (PAOs) have biodegradability in the 5-30% range. Organic compounds with low biodegradability (i.e. less than about 40% biodegradability) are said to bioaccumulate. Bioaccumulation tends to magnify the toxic effect of chemicals on the environment.

Hydroisomerization of Bio-Based Paraffins: The HDO paraffins may be subjected to hydroisomerization to provide a hydroisomerized product. The hydroisomerized product includes methyl-branched paraffins in the $C_{16}$-$C_{18}$ range with low pour point, high thermal/oxidative stability, and low ecotoxicity. Hydroisomerization is conducted over a bifunctional catalyst at temperatures in the range of about 200° C. to about 500° C. The hydroisomerization may be conducted at a temperature of about 220° C., about 240° C., about 260° C., about 280° C., about 300° C., about 320° C., about 340° C., about 360° C., about 380° C., about 400° C., about 420° C., about 440° C., about 460° C., about 480° C., and ranges between any two of these values or above any one of these values. Bifunctional catalysts are those having a hydrogenation-dehydrogenation activity from a Group VIB and/or Group VIII metal, and acidic activity from an amorphous or crystalline support such as amorphous silica-alumina (ASA), silicon-aluminum-phosphate (SAPO) molecular sieve, or aluminum silicate zeolite (ZSM). In some embodiments, the hydroisomerization catalysts include Pt/Pd-on-ASA, and Pt-on-SAPO-11.

In some embodiments, hydroisomerization is conducted in continuous fixed-bed reactors. In such embodiments, the hydrogen partial pressure for hydroisomerization is in the range between about 30 bar and about 160 bar, GORs are in the range of about 100 NL/L to about 1,000 NL/L, and LHSV in the range from about 0.2 hr$^{-1}$ to about 5 hr$^{-1}$. In some embodiments, the hydrogen partial pressure for hydroisomerization is about 40 bar, about 50 bar, about 60 bar, about 70 bar, about 80 bar, about 90 bar, about 100 bar, about 110 bar, about 120 bar, about 130 bar, about 140 bar, about 150 bar, and ranges between any two of these values or above any one of these values. In some embodiments, the GOR may be about 150 NL/L, about 200 NL/L, about 250 NL/L, 300 NL/L, 350 NL/L, 400 NL/L, 450 NL/L, 500 NL/L, 550 NL/L, 600 NL/L, 650 NL/L, 700 NL/L, 750 NL/L, 800 NL/L, 850 NL/L, 900 NL/L, 950 NL/L, and ranges between any two of these values or above any one of these values. The LHSV may be about 0.3 h$^{-1}$, about 0.4 h$^{-1}$, about 0.5 h$^{-1}$, about 0.6 h$^{-1}$, about 0.7 h$^{-1}$, about 0.8 h$^{-1}$, about 0.9 h$^{-1}$, about 1.0 h$^{-1}$, about 1.2 h$^{-1}$, about 1.4 h$^{-1}$, about 1.6 h$^{-1}$, about 1.8 h$^{-1}$, about 2.0 h$^{-1}$, about 2.2 h$^{-1}$, about 2.4 h$^{-1}$, about 2.6 h$^{-1}$, about 2.8 h$^{-1}$, about 3.0 h$^{-1}$, about 3.0 h$^{-1}$, about 3.2 h$^{-1}$, about 3.4 h$^{-1}$, about 3.6 h$^{-1}$, about 3.8 h$^{-1}$, about 4.0 h$^{-1}$, about 4.2 h$^{-1}$, about 4.4 h$^{-1}$, about 4.6 h$^{-1}$, about 4.8 h$^{-1}$, and ranges between any two of these values or above any one of these values.

In an embodiment, the HDO product is hydroisomerized according to the conditions described herein using Pt/SAPO-11 catalyst. The hydroisomerizate is preferably stripped of light hydrocarbons in order to raise the flash point above 60° C. The flash point may be above 70° C., above 80° C., above 90° C., or above 100° C. The hydroisomerized product has a ratio of isoparaffins-to-normal paraffins in the range of about 1:1 to about 30:1. The ratio of isoparaffins-to-normal paraffins may be about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, and ranges between any two of these values or above any one of these values. In some embodiments, the ratio of isoparaffins-to-normal paraffins is between about 5:1 and about 20:1. In the hydroisomerized product at least 80 wt % of the isoparaffins are mono-methyl branched paraffins. The mono-methyl branched paraffins may be about 81 wt %, about 82 wt %, about 83 wt %, about 84 wt %, about 85 wt %, about 86 wt %, about 87 wt %, about 88 wt %, about 89 wt %, about 90 wt %, about 91 wt %, about 92 wt %, about 93 wt %, about 94 wt %, about 95 wt %, about 96 wt %, about 97 wt %, about 98 wt %, about 99 wt %, and ranges between any two of these values or above any one of these values. Examples of the mono-methyl branched paraffins in the hydroisomerized HDO product include 4-methyl heptadecane, 3-methyl hexadecane, and 2-methyl pentadecane. Of the mono-methyl branched isoparaffins, less than 30 wt % are terminal branched (i.e. 2-methyl branched). In some embodiments, less than 20 wt % of the mono-methyl branched isoparaffins are terminal branched. In some embodiments, less than 15 wt % of the mono-methyl branched isoparaffins are terminal branched. In some embodiments, less than 10 wt % of the mono-methyl branched isoparaffins are terminal branched. In some embodiments, less than 5 wt % of the mono-methyl branched isoparaffins are terminal branched. It is important to note that the method does not involve more severe aromatic hydrogenation conditions.

The isoparaffins have a biodegradability of at least about 40% after about 23 days of exposure to microorganisms. The biodegradability may be about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, and ranges between any two of these values or greater than any one of these values. The isoparaffins have a kinematic viscosity of less than about 10 cSt at 40° C. The isoparaffins may have a kinematic viscosity at 40° C. of about 9 cSt, about 8 cSt, about 7 cSt, about 6 cSt, about 5 cSt, about 4 cSt, about 3 cSt, about 2 cSt, about 1 cSt, and ranges in between any two of these values or below any one of these values.

The hydroisomerized product may contain aromatics in the amount of about 0.9 wt %, about 0.8 wt %, about 0.7 wt %, about 0.6 wt %, about 0.5 wt %, about 0.4 wt %, about 0.3 wt %, about 0.2 wt %, about 0.1 wt %, and ranges between any two of these values or below any one of these values. In some embodiments, the hydroisomerized product contains less than 0.1 wt % total aromatics. In some embodiments, the hydroisomerized product is free of benzene. The hydroisomerized product has a kinematic viscosity of less than about 10 cSt at 40° C. The hydroisomerized product has a kinematic viscosity of less than about 10 cSt at 40° C. The hydroisomerized product may have a kinematic viscosity at 40° C. of about 9 cSt, about 8 cSt, about 7 cSt, about 6 cSt, about 5 cSt, about 4 cSt, about 3 cSt, about 2 cSt, about 1 cSt, and ranges in between any two of these values or below any one of these values.

Due the presence of mostly internal mono-methyl branched paraffins, the hydroisomerized HDO product of this technology has an excellent balance of properties for use as drilling and/or hydraulic fracturing fluids. The pour point of the hydroisomerized fluid of this embodiment is at most –10° C. The pour point may be at most about –15° C., at least about –20° C., at most about –25° C., at most about –30° C., at most about –35° C., at most about –40° C., or at most about –45° C. The thermo-oxidative stability of the fluid may be measured by amount of insolubles formed upon heating and reported as mg/100 mL according to ASTM D2274. For example, the stability thus measured can be as high as 20 mg/100 mL for fluids with inferior oxidative stability properties, such as fatty acid esters. The lower the concentration of insolubles formed, the higher the thermo-oxidative stability of the fluid. The ASTM D2274 oxidative stability of the fluid produced by hydroisomerization of the HDO product as described herein is between about 0 mg/100 mL and about 2 mg/100 mL upon addition of up to 20 wppm anti-oxidant. Preferred anti-oxidants for the bio-based hydrocarbon fluids of this technology are hindered phenols, such as butyrated hydroxy toluene (BHT). Other examples of suitable anti-oxidants for the bio-based synthetic hydrocarbon fluids of this invention include 2,4-dimethyl-6-t-butylphenol, 2,6-di-t-butyl-4-methylphenol, 2- and 3-t-butyl-4-hydroxyanisol (BHA), 2,6-distyrenated p-cresol, 2,6-di-t-butylphenol, 2,6-di-t-butyl-4-sec-butylphenol, 2,6-di-t-butyl-4-nonylphenol, 2,4-bis-(n-octylthio)-6-(4-hydroxy-3',5'-di-t-butylanilino)-

1,3,5-triazine, 2,4-bis-(octylthiomethyl)-6-methylphenol, 2,6-di-t-butyl-4-ethylphenol, 2,4-dimethyl-6-t-butylphenol, the butylated reaction product of p-cresol and dicylcopentadiene, the mixed methylenic bridged adducts of alkylated phenol and dodecane thiol, tetrakis methylene (3,5-di-t-butyl-4-hydroxyhydrocinnamate) methane, 1,3,5-trimethyl-2,4,6-tris(3,5-di-t-butyl-4-hydroxybenzyl)benzene, tris(3,5-di-t-butyl-4-hydroxybenzyl) isocyanurate, and mixtures of any two or more thereof of the recited anti-oxidants.

Chlorinating Bio-Based Paraffins: Paraffin chlorination according to the present technology is one way of increasing the viscosity of a paraffinic fluid while reducing crystallinity and hence lowering the paraffin pour point. For example, the HDO product does not have the required viscosity and pour point for use, by itself, in such industrial processing fluid applications as metal-working.

The HDO product and/or the hydroisomerized product may be chlorinated in a batch reactor by sparging pure chlorine gas into the liquid at a temperature in the range between about 60° C. and about 150° C. The temperature of the chlorination reaction may be about 65° C., about 70° C., about 80° C., about 85° C., about 90° C., about 95° C., about 100° C., about 105° C., about 110° C., about 115° C., about 120° C., about 125° C., about 130° C., about 140° C., about 145° C., and ranges in between any two of these values or greater than any one of these values. In some embodiments, the temperature is in the range between about 80° C. and about 120° C. Chlorination is an exothermic reaction and cooling is necessary. Generally catalysts are not necessary at these temperatures, but in some embodiments UV light is used to accelerate the reaction. Once the desired degree of chlorination, typically between about 30 wt % and about 70 wt %, and viscosity has been achieved, the chlorine supply is discontinued and the reactor purged with air or nitrogen to remove excess chlorine and hydrochloric acid gas. Hydrochloric acid is a co-product of the paraffin chlorination process.

The chlorinated paraffins, i.e. the chlorinated product, can be used as an industrial process fluid for metal-working lubricants, as plasticizers, flame-retardants, and fat liquors for leather. Plasticizers are generally used to make rigid polymers like PVC soft and rubbery. Addition of chlorinated paraffins also imparts flame-retardancy to the polymer compound. Fat liquors are fluids that are used to improve the life and appearance of articles made of leather, such as jackets, handbags, and shoes. In some embodiments, the chlorinated product is used as a protecting agent, a cleaning agent, or a combination of both. In some embodiments, the chlorinated product acts as a flame retardant. In some embodiments, the chlorinated product is used to clean fabric, metal, or plastic.

The chlorinated product has a kinematic viscosity of greater than about 10 cSt at 40° C. The chlorinated product may have a kinematic viscosity at 40° C. of about 12 cSt, about 14 cSt, about 16 cSt, about 18 cSt, about 20 cSt, about 22 cSt, about 24 cSt, about 26 cSt, about 28 cSt, about 30 cSt, and ranges in between any two of these values or greater than any one of these values. In some embodiments, the oligomerized product has a kinematic viscosity greater than about 20 cSt at 40° C. The chlorinated product is between about 30 wt % and about 70 wt % chlorine in the form of chlorine covalently bound to carbon. The amount of covalently bonded chlorine in the chlorinated product may be about 35 wt %, about 40 wt %, about 45 wt %, about 50 wt %, about 55 wt %, about 60 wt %, about 65 wt %, and ranges between any two of these values or greater than any one of these values. The chlorinated product has less than about 1 wt % aromatics. The chlorinated product may contain aromatics in the amount of about 0.9 wt %, about 0.8 wt %, about 0.7 wt %, about 0.6 wt %, about 0.5 wt %, about 0.4 wt %, about 0.3 wt %, about 0.2 wt %, about 0.1 wt %, and ranges between any two of these values or below any one of these values. In some embodiments, the chlorinated product contains less than 0.1 wt % total aromatics. In some embodiments, the chlorinated product is free of benzene. In some embodiments, the chlorinated product is used as a protecting agent, a cleaning agent, or a combination of both. In some embodiments, the chlorinated product acts as a flame retardant. In some embodiments, the chlorinated product is used to clean fabric, metal, or plastic.

Dehydrochlorination of Bio-Derived Paraffins: The chlorinated products may optionally be subjected to dehydrochlorination, wherein the chlorine is removed as hydrochloric acid. As an example, in embodiments where the chlorinated product is exclusively made from the HDO product, dehydrochlorination yields a linear olefin composition having a carbon number range similar to the HDO paraffin. The dehydrochlorination reaction takes place over silica or bauxite at temperatures in the 360° C.-700° C. range. The reaction may take place at a temperature of about 380° C., about 400° C., about 420° C., about 440° C., about 460° C., about 480° C., about 500° C., about 550° C., about 600° C., about 650° C., and ranges in between any two of these values or above any one of these values. In some embodiments, the reaction takes place at temperature in the range from about 400° C. to about 600° C. Dehydrochlorination may proceed in the range from about 68% conversion to about 100% conversion. Dehydrochlorination can proceed to about 70% conversion, about 75% conversion, about 80% conversion, about 85% conversion, about 90% conversion, about 95% conversion, about 98% conversion, about 99% conversion, and ranges in between any two of these values or above any one of these values. As such, the dehydrochlorination reactor product from dehydrochlorination of the HDO product is a $C_{16}/C_{18}$ linear hydrocarbon composition comprising up to 100% internal olefins, characterized by higher biodegradability than saturated hydrocarbons. This olefinic composition has a lower pour point and higher lubricity than the equivalent paraffin composition, making it particularly well-suited for drilling and hydraulic fracturing fluid formulations.

The olefinic composition has a biodegradability of at least about 40% after about 23 days of exposure to microorganisms. The biodegradability may be about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, and ranges between any two of these values or greater than any one of these values. The olefinic composition has a kinematic viscosity of less than about 10 cSt at 40° C. The olefinic composition may have a kinematic viscosity at 40° C. of about 9 cSt, about 8 cSt, about 7 cSt, about 6 cSt, about 5 cSt, about 4 cSt, about 3 cSt, about 2 cSt, about 1 cSt, and ranges in between any two of these values or below any one of these values. The olefinic composition may contain aromatics in the amount of about 0.9 wt %, about 0.8 wt %, about 0.7 wt %, about 0.6 wt %, about 0.5 wt %, about 0.4 wt %, about 0.3 wt %, about 0.2 wt %, about 0.1 wt %, and ranges between any two of these values or below any one of these values. In some embodiments, the olefinic composition contains less than 0.1 wt % total aromatics. In some embodiments, the olefinic composition is free of benzene. In some embodiments, the olefinic composition is used as a hydraulic fracturing fluid, as a drilling fluid, or a combination of the two.

Dehydrogenation of Bio-Derived Paraffins: The paraffinic fluid, for example the HDO product and/or the hydroisomerization product, may be subjected to dehydrogenation to produce a olefinic fluid with an improved balance of biodegradability, lubricity, thermo-oxidative stability, ecotoxicity, and pour point, for drilling base fluids. The reaction takes place at a temperature in the range from about 360° C. to about 660° C. The reaction may take place at about 380° C., about 400° C., about 420° C., about 440° C., about 460° C., about 480° C., about 500° C., about 520° C., about 540° C., about 560° C., about 580° C., about 600° C., about 620° C., about 640° C., and ranges between any two of these values or above any one of these values. In some embodiments, the reaction takes place in a temperature in the range from about 440° C. to about 580° C. The reaction is endothermic and is favored at low pressures. Typical operating pressures are in the range from about 1 bar to about 20 bar. The operating pressure may be about 2 bar, about 3 bar, about 4 bar, about 5 bar, about 6 bar, about 7 bar, about 8 bar, about 9 bar, about 10 bar, about 11 bar, about 12 bar, about 13 bar, about 14 bar, about 15 bar, about 16 bar, about 17 bar, about 18 bar, about 19 bar, and ranges between any two of these values or above any one of these values. In some embodiments, the operating pressure is from about 2 bar to about 12 bar. At these conditions, the hydrocarbons are in vapor phase. Generally base metals and noble metal catalysts from Groups VIB and VIII that have hydrogenation-dehydrogenation activity provide a low activation energy mechanism for paraffin dehydrogenation. Such metals include Pt, Pd, Rh, Ru, Ir, Os, and Re. The reaction is carried out in gas phase at high temperatures and low pressures. Preferred catalyst systems for paraffin dehydrogenation include alkali and alkaline earth metal promoters as well. A preferred catalyst for the system is platinum/lithium on alumina.

In an embodiment, the HDO paraffins are pressurized to about 10 bar and preheated to about 580° C. before entering a dehydrogenation reactor. It is important to note that the conditions provided in this embodiment are applicable to the dehydrogenation of the hydroisomerized product described earlier. The reactor is packed with Pt/Li-on-alumina catalyst. The reactor geometry is selected to provide low pressure drop while ensuring sufficient contact time to achieve desired conversion, and preferably approach the thermodynamic equilibrium conversion for the endothermic reactions. Preferred contact times are expressed by liquid hourly space velocities (LHSV) in the range of about $1\ h^{-1}$ to about $10\ h^{-1}$. The LHSV may be about $1.2\ h^{-1}$, about $1.4\ h^{-1}$, about $1.6\ h^{-1}$, about $1.8\ h^{-1}$, about $2.0\ h^{-1}$, about $2.2\ h^{-1}$, about $2.4\ h^{-1}$, about $2.6\ h^{-1}$, about $2.8\ h^{-1}$, about $3.0\ h^{-1}$, about $3.0\ h^{-1}$, about $3.2\ h^{-1}$, about $3.4\ h^{-1}$, about $3.6\ h^{-1}$, about $3.8\ h^{-1}$, about $4.0\ h^{-1}$, about $4.2\ h^{-1}$, about $4.4\ h^{-1}$, about $4.6\ h^{-1}$, about $4.8\ h^{-1}$, about $5.0\ h^{-1}$, about $5.2\ h^{-1}$, about $5.4\ h^{-1}$, about $5.6\ h^{-1}$, about $5.8\ h^{-1}$, about $6.0\ h^{-1}$, about $6.2\ h^{-1}$, about $6.4\ h^{-1}$, about $6.6\ h^{-1}$, about $6.8\ h^{-1}$, about $7.0\ h^{-1}$, about $7.2\ h^{-1}$, about $7.4\ h^{-1}$, about $7.6\ h^{-1}$, about $7.8\ h^{-1}$, about $8.0\ h^{-1}$, about $8.2\ h^{-1}$, about $8.4\ h^{-1}$, about $8.6\ h^{-1}$, about $8.8\ h^{-1}$, about $9.0\ h^{-1}$, about $9.2\ h^{-1}$, about $9.4\ h^{-1}$, about $9.6\ h^{-1}$, about $9.8\ h^{-1}$, and ranges between any two of these values or above any one of these values. It should be noted that although space velocities are expressed in terms of liquid feed, in some embodiments of the dehydrogenation conditions the reactor feed and products are in the vapor phase. In some embodiments, a plurality of reactors is configured in series, with provisions for heating each reactor feed. In some embodiments, between about 5 wt % and about 40 wt % of the HDO n-paraffins are converted to linear olefins. The conversion of HDO n-paraffins to linear olefins may be about 10 wt %, about 15 wt %, about 20 wt %, about 25 wt %, about 30 wt %, about 35 wt %, and ranges in between any two of these values or above any one of these values. In some embodiments, between about 10 wt % and about 30 wt % of the HDO n-paraffins are converted to linear olefins. The reactor effluent is cooled to condense a linear hydrocarbon product composition from hydrogen, where the linear hydrocarbon product composition is primarily in the $C_{16}$-$C_{18}$ range. The hydrogen may be partially recycled to the reactor to mitigate coking in the reactor. A hydrogen-to-hydrocarbon mole ratio of about 1:1 to about 20:1 is utilized. The hydrogen-to-hydrocarbon mole ratio may be about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, and ranges between any two of these values or above any one of these values. In some embodiments, the hydrogen-to-hydrocarbon mole ratio is from about 8:1 to about 12:1.

The liquid product of this embodiment of the dehydrogenation of the HDO product is a straight-chain hydrocarbon composition comprising of n-paraffins and linear olefins. The composition comprises 50-90 wt % n-paraffins in the $C_{16}$-$C_{18}$ range, 10-40 wt % $C_{16}$-$C_{18}$ linear internal olefins in the $C_{16}$-$C_{18}$ range, and 0-10 wt % linear alpha olefins in the $C_{16}$-$C_{18}$ range. The composition may have n-paraffins in the $C_{16}$-$C_{18}$ range in the amount of about 55 wt %, about 60 wt %, about 65 wt %, about 70 wt %, about 75 wt %, about 80 wt %, about 85 wt %, and ranges in between any two of these values or below any one of these values. The composition may have linear internal olefins in the $C_{16}$-$C_{18}$ range in the amount of about 15 wt %, about 20 wt %, about 25 wt %, about 30 wt %, about 35 wt %, and ranges between any two of these values or above any one of these values. The composition may have linear alpha olefins in the $C_{16}$-$C_{18}$ range in the amount of about 0 wt % to about 5 wt % or about 5 wt % to about 10 wt %.

Due the presence of linear internal olefins, the pour point of the straight-chain hydrocarbon composition is lowered. Compared to fully saturated hydrocarbons, this composition offers superior biodegradability, making it attractive as a drilling base fluid.

The olefinic fluid has a biodegradability of at least about 40% after about 23 days of exposure to microorganisms. The biodegradability may be about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, and ranges between any two of these values or greater than any one of these values. The olefinic fluid has a kinematic viscosity of less than about 10 cSt at 40° C. The olefinic fluid may have a kinematic viscosity at 40° C. of about 9 cSt, about 8 cSt, about 7 cSt, about 6 cSt, about 5 cSt, about 4 cSt, about 3 cSt, about 2 cSt, about 1 cSt, and ranges in between any two of these values or below any one of these values. The olefinic fluid of the present technology may contain aromatics in the amount of about 0.9 wt %, about 0.8 wt %, about 0.7 wt %, about 0.6 wt %, about 0.5 wt %, about 0.4 wt %, about 0.3 wt %, about 0.2 wt %, about 0.1 wt %, and ranges between any two of these values or below any one of these values. In some embodiments, the olefinic fluid contains less than 0.1 wt % total aromatics. In some embodiments, the olefinic fluid is free of benzene. In some embodiments, the olefinic fluid is used as a hydraulic fracturing fluid, as a drilling fluid, or a combination of the two.

Acid-Catalyzed Oligomerization: It is to be understood that the term "oligomerization" as used herein refers to the formation of a compound from 2, 3, 4, 5, 6, 7, 8, 9 or 10 monomers, where the compound formed by oligomerization is an "oligomer" or an "oligomerized product." For example, a dimer is a compound made from the oligomerization of 2 monomers, a trimer is a compound made from the oligomerization of 3 monomers, and a tetramer is a compound made from the oligomerization of 4 monomers. The olefins produced by dehydrogenation of the bio-derived paraffins or by dehydrochlorination of the chlorinated product, described above, can be oligomerized to produce fluids having a higher average molecular weight, higher boiling range, and higher viscosity. Since most of the carbon-carbon double bonds in the linear olefins are mainly in the internal positions (as indicated in the aforementioned section describing the internal olefins), the branched dimers are characterized by mainly $C_2$+ chain branching. Such fluids, having a kinematic viscosity greater than about 10 cSt at 40° C. are excellently suited for various mineral oil and lubricating oil applications. The oligomerized product may have a kinematic viscosity at 40° C. of about 12 cSt, about 14 cSt, about 16 cSt, about 18 cSt, about 20 cSt, about 22 cSt, about 24 cSt, about 26 cSt, about 28 cSt, about 30 cSt, and ranges in between any two of these values or greater than any one of these values. In some embodiments, the oligomerized product has a kinematic viscosity greater than about 20 cSt at 40° C.

Acids for olefin oligomerization include, but are not limited to, Lewis acids such as boron trifluoride and aluminum trichloride. Heterogeneous catalysts such as zeolites are another class of catalysts for olefin oligomerization. The reactions are conducted in a continuous stirred tank reactor using between about 1 wt % and about 15 wt % of the Lewis acid catalyst based on a oligomerization reactor hydrocarbon feed basis. The Lewis acid catalyst may be at about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, and ranges between any two of these values. In some embodiments, the Lewis acid catalyst is from about 2 wt % to about 8 wt %. The reactor operates at a temperature in about the 0° C. to 200° C. range, under about 1 bar to about 10 bar pressure. The reactor may operate at a temperature of about 10° C., about 20° C., about 30° C., about 40° C., about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., and ranges in between any two of these values. In some embodiments, the temperature is from about 20° C. to about 120° C. The reactor may operate at a pressure of about 2 bar, about 3 bar, about 4 bar, about 5 bar, about 6 bar, about 7 bar, about 8 bar, about 9 bar, and ranges in between any two of these values or above any one of these values. Reactor residence times are in the range of about 20 minutes to about 120 minutes. The reactor residence time may be about 30 minutes, about 40 minutes, about 50 minutes, about 60 minutes, about 70 minutes, about 80 minutes, about 90 minutes, about 100 minutes, about 110 minutes, and ranges in between any two of these values. In some embodiments, the reactor residence time is from about 30 minutes to about 90 minutes. The reactor effluent includes products of the oligomerization reaction. Unreacted hydrocarbons, if present, may be separated from the oligomerized product. The oligomerization product is predominately dimers and tetramers of the linear internal olefins. In some embodiments, the dimers and tetramers are greater than 60 wt % of the oligomerized product. The oligomerization product of this embodiment includes long-chain branched hydrocarbons. The unreacted linear hydrocarbons include the paraffin feed to the dehydrogenation reactor and the olefinic fluid not reacted under acid-catalyzed oligomerization conditions.

The oligomerized product may include a dimer, trimer, tetramer, or a mixture of any two or more thereof. The oligomerized product of the present technology may contain aromatics in the amount of about 0.9 wt %, about 0.8 wt %, about 0.7 wt %, about 0.6 wt %, about 0.5 wt %, about 0.4 wt %, about 0.3 wt %, about 0.2 wt %, about 0.1 wt %, and ranges between any two of these values or below any one of these values. In some embodiments, the oligomerized product contains less than 0.1 wt % total aromatics. In some embodiments, the oligomerized product is free of benzene. The oligomerized product has a biodegradability of at least about 40% after about 23 days of exposure to microorganisms. The biodegradability may be about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, and ranges between any two of these values or greater than any one of these values. In some embodiments, the oligomerized product is used as a drilling fluid, a hydraulic fracturing fluid, a metal working fluid, a protecting agent, or a combination of any two or more thereof.

Peroxide-Initiated Oligomerization: Organic peroxide treatment may be used to initiate oligomerization of HDO and/or hydroisomerized HDO products. As stated above, it is to be understood that the term "oligomerization" as used herein refers to the formation of a compound from 2, 3, 4, 5, 6, 7, 8, 9 or 10 monomers, where the compound formed by oligomerization is an "oligomer." For example, a dimer is a compound made from the oligomerization of 2 monomers, a trimer is a compound made from the oligomerization of 3 monomers, and a tetramer is a compound made from the oligomerization of 4 monomers. The product composition, comprising dimers and co-dimers of the linear and/or branched paraffins, has a kinematic viscosity greater than about 10 cSt at 40 C. The product is thus well suited for use in various mineral oil and lubricating oil applications.

Organic peroxides generate free radicals that extract hydrogen atoms from secondary and tertiary carbons of the paraffinic hydrocarbons, providing free radical sites therein for subsequent coupling reactions. The organic peroxides for the reaction are of the formula R—O—O—R' where R and R' are each independently H, alkyl, or aryl. In some embodiments, organic peroxides for the reaction include dialkyl peroxides including, but not limited to, di-tert butyl peroxide (DTBP), 2,5-dimethyl 2,5-di(t-butylperoxy)hexane, dicumyl peroxide, dibenzoyl peroxide, dipropyl peroxide, ethyl propyl peroxide, tert-butyl tert-amyl peroxide, or combinations of any two or more thereof.

Peroxide-initiated oligomerization may be carried out in batch or continuous reactors. Preferred batch reactor embodiments are agitated tanks with provisions for heat transfer/temperature control. These include jackets, internal coils, or pump-around heat exchange. Continuous flow reactors include those approaching plug-flow behavior such as tubular reactors (including, but not limited to, static mixers) and fixed-bed vessels packed with inert media like ceramic balls. As with the batch reactors, these plug-flow reactors may include provisions for heat transfer/temperature control. A low capital cost embodiment of the continuous reactor for peroxide-initiated oligomerization is the jacketed pipe or the pipe-in-pipe reactor.

The reactor feed comprising HDO and/or hydroisomerized HDO paraffins includes between about 2 wt % and about 40 wt % organic peroxide and the reactor is controlled at a temperature from about 50° C. to about 250° C. The organic peroxide may be in the amount of about 3 wt %, about 4 wt %, about 5 wt %, about 6 wt %, about 7 wt %, about 8 wt %, about 9 wt %, about 10 wt %, about 12 wt %, about 14 wt %, about 16 wt %, about 18 wt %, about 20 wt %, about 22 wt %, about 24 wt %, about 26 wt %, about 28 wt %, about 30 wt %, about 32 wt %, about 34 wt %, about 36 wt %, about 38 wt %, and ranges between any two of these values or above any one of these values. In some embodiments, the organic peroxide is in the amount of about 5 wt % to about 20 wt %. The reactor temperature may be about 60° C., about 70° C., about 80° C., about 90° C., about 100° C., about 110° C., about 120° C., about 130° C., about 140° C., about 150° C., about 160° C., about 170° C., about 180° C., about 190° C., about 200° C., about 210° C., about 220° C., about 230° C., about 240° C., and ranges in between any two of these values. In some embodiments, the temperature is between about 70° C. and about 200° C. The reactor is controlled at a suitable pressure, high enough to ensure reactor contents are in liquid phase. This pressure is typically from about 1 bar to about 10 bar. The reactor may operate at a pressure of about 2 bar, about 3 bar, about 4 bar, about 5 bar, about 6 bar, about 7 bar, about 8 bar, about 9 bar, and ranges in between any two of these values or above any one of these values. Batch cycle times, or residence times of continuous flow reactors, are in the range from about 10 minutes to about 120 minutes. The reactor residence time may be about 10 minutes, about 20 minutes, about 30 minutes, about 40 minutes, about 50 minutes, about 60 minutes, about 70 minutes, about 80 minutes, about 90 minutes, about 100 minutes, about 110 minutes, and ranges in between any two of these values. In some embodiments, the reactor residence time is from about 20 minutes to about 90 minutes.

In the batch mode, all the peroxide may be charged at once following addition of the paraffinic feedstock. The peroxide may also be introduced in increments over the batch cycle time. In other embodiments of peroxide-initiated oligomerization, the organic peroxide is fed to the batch reactor continuously during all or a portion of the batch reaction cycle time, preferably using a metering pump or control valve. This mode of operation is also referred to as "semi-batch" in the art.

The reactor effluent comprises oligomerization products, mainly dimers and trimers of the HDO and/or hydroisomerization paraffins. The unreacted paraffins, making up between about 0 wt % and about 60 wt % of the effluent composition, are optionally stripped (preferably via atmospheric or vacuum distillation) to yield a oligomerized fluid product having a kinematic viscosity greater than about 10 cSt at 40° C. The oligomerized product may have a kinematic viscosity at 40° C. of about 12 cSt, about 14 cSt, about 16 cSt, about 18 cSt, about 20 cSt, about 22 cSt, about 24 cSt, about 26 cSt, about 28 cSt, about 30 cSt, and ranges in between any two of these values or greater than any one of these values. In some embodiments, the oligomerized product has a kinematic viscosity greater than about 20 cSt at 40° C. This product is well-suited for use in various lubricating applications where a combination of high thermal stability, low ecotoxicity, and good low temperature properties is desired. The unreacted paraffins in the effluent composition may be about 1 wt %, about 2 wt %, 3 wt %, about 4 wt %, about 5 wt %, about 6 wt %, about 7 wt %, about 8 wt %, about 9 wt %, about 10 wt %, about 12 wt %, about 14 wt %, about 16 wt %, about 18 wt %, about 20 wt %, about 22 wt %, about 24 wt %, about 26 wt %, about 28 wt %, about 30 wt %, about 32 wt %, about 34 wt %, about 36 wt %, about 38 wt %, about 40 wt %, about 50 wt % and ranges between any two of these values or above any one of these values.

The oligomerized product may include a dimer, trimer, tetramer, or a mixture of any two or more thereof. The oligomerized product has a biodegradability of at least about 40% after about 23 days of exposure to microorganisms. The biodegradability may be about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, and ranges between any two of these values or greater than any one of these values. The oligomerized product of the present technology may contain aromatics in the amount of about 0.9 wt %, about 0.8 wt %, about 0.7 wt %, about 0.6 wt %, about 0.5 wt %, about 0.4 wt %, about 0.3 wt %, about 0.2 wt %, about 0.1 wt %, and ranges between any two of these values or below any one of these values. In some embodiments, the oligomerized product contains less than 0.1 wt % total aromatics. In some embodiments, the oligomerized product is free of benzene. In some embodiments, the oligomerized product is used as a drilling fluid, a hydraulic fracturing fluid, a metal working fluid, a protecting agent, or a combination of any two or more thereof.

In another aspect, a method is provided involving protecting a substance by applying the above-described paraffinic fluids. In the method, the paraffinic fluid includes a hydrodeoxygenated product; where the hydrodeoxygenated product is produced by hydrodeoxygenating a bio-derived feed; the bio-derived feed comprises bio-derived fatty acids, fatty acid esters, or a combination thereof the hydrodeoxygenated product comprises n-paraffins; the paraffinic fluid contains less than 1 wt % aromatics; and the n-paraffins have a kinematic viscosity of less than about 10 cSt at 40° C. and have a biodegradability of at least 40% after about 23 days of exposure to microorganisms. In some embodiments, the hydrodeoxygenated product includes n-paraffins in the range of about 80 wt % to about 100 wt %; cycloparaffins in the range of about 0 wt % to about 10 wt %; less than about 1 wt % total aromatics. In some embodiments, the paraffinic fluid further includes a hydroisomerized product produced by at least partially hydroisomerizing the hydrodeoxygenated product; where the hydroisomerized product comprises isoparaffins where at least about 80 wt % of the isoparaffins are monomethyl branched paraffins; the mono-methyl branched paraffins comprise less than about 30 wt % terminal branched isoparaffins; and the isoparaffins have a kinematic viscosity of less than about 10 cSt at 40° C. and have a biodegradability of at least about 40% after about 23 days of exposure to microorganisms.

Thus, in some embodiments of the method, the substance is a food crop, a metal, or wood. In some embodiments, protecting involves solvating the substance. In such embodiments, the substance includes pesticides, herbicides, paints, inks, or coatings. In some embodiments of the method, protecting involves cleaning the substance with the paraffinic fluid In such embodiments, the substance comprises fabric, metal, or plastic. In some embodiments of the method, protecting involves lubricating the substance where the substance is metal. Such a method is exemplified by the protecting applications listed for dry cleaning fluids, industrial solvents, crop protection solvents/coating oils, grain de-dusting oils, metal working fluids, industrial cleaning fluids, lubricating base oils, polymerization fluids, transformer oils, cosmetic oils, food preparation oils, and drilling fluids and hydraulic fracturing fluids of the present technology.

Dry Cleaning Fluids: Bio-based synthetic fluids of this technology may be used as a substitute for petroleum-based solvents and perchloroethylene for dry cleaning of apparel. These fluids comprise hydrocarbons in the $C_{10}$-$C_{15}$ range. The paraffinic nature of the fluid (specifically its non-corrosive, non-polar properties) allows it to be used with many sensitive fabrics. They remove oil and grease effectively, aid in removing water-soluble dirt when combined with effective detergents, and are virtually odorless. The kinematic viscosities of these fluids are less than 10 cSt at 40° C. For reducing risk of fire, the flash point is generally above 38° C. Dry cleaning fluids of this technology include hydrocarbons in the $C_{10}$-$C_{15}$ range.

Industrial Solvents: Bio-based synthetic fluids of this technology may be used as solvents for paints, inks, adhesives, and coatings. These fluids comprise paraffinic hydrocarbons in the $C_5$-$C_{20}$ range. Due to virtual absence of aromatic hydrocarbons and odors, these fluids meet increasingly stringent regulatory requirements. The bio-based synthetic fluids are characterized by selective solvency as characterized by an aniline number greater than about 80° C., and a Kauri-Butanol value greater than about 19. They are an effective substitute for petroleum-based solvents, including ISOPAR® and SOLTROL® products. (ISOPAR® and SOLTROL® are trademarks of ExxonMobil Chemical and Chevron Phillips Chemical respectively.) The viscosities of these fluids are less than about 10 cSt at 40° C., with volatility (flash point and distillation/boiling range) adjusted according to the specific application. As such, the lighter hydrocarbons, such as those in the $C_5$-$C_7$ range, may be stripped/distilled in order to provide industrial solvents having higher flash points and thus with a reduced risk of fire.

Crop Protection Solvents/Coating Oils: Bio-based synthetic fluids of this technology may be used as agricultural solvents and spray oils. These fluids include paraffinic hydrocarbons in the $C_5$-$C_{20}$ range for solvent applications (e.g. for dissolving pesticides and herbicides), and in the $C_{16}$-$C_{36}$ range for coating oil applications. Examples of crop protection solvent applications include dissolving and spraying pesticides. These include applications where the solvent is used to extract a natural herbicide for crop protection. In these cases, selective solvency, as indicated by an aniline number greater than about 80° C., and a Kauri-Butanol value greater than about 19, is a key attribute of the paraffinic solvent.

When used as coating oil, the fluid is applied to the plant leaves forming a film that protects the plant from fungi and pests. Because the coating oil is a non-toxic chemical, as defined by an eco-toxicity where $LC_{50}$>3.5 mg/L (as described above), the pests cannot become immune to the product. The spray oil naturally bio-degrades and evaporates during the growth cycle of the plant. And because the bio-based fluids are naturally free-of sulfur, they do not leave a sulfonic residue. Typically, for coating oil applications, the fluid viscosity is greater than about 10 cSt at 40° C.

Grain De-Dusting Oil: This application is similar to the crop protection coating oil. Bio-based synthetic fluids of the present technology that include hydrocarbons in the $C_{16}$-$C_{36}$ range provide the required performance, mitigating dust accumulation when handling grain. For this application, fluid viscosity is greater than about 10 cSt at 40° C.

Metal Working Fluids: Bio-based synthetic fluids of this technology may be used as metal working fluids, including metal lubricating and metal rolling fluids. For applications such as aluminum rolling (e.g. for preparing rolls of aluminum foils) paraffinic hydrocarbons in the $C_{11}$-$C_{20}$ range, having kinematic viscosities less than about 10 cSt at 40° C. and flash points above about 60° C. are most suitable.

For applications involving more severe metal-metal contact where lubricating properties are desired, chlorinated paraffins from chlorination of the HDO product as described above, or bio-derived synthetic fluids of the present technology having a carbon number in the $C_{16}$-$C_{36}$ range and a kinematic viscosity greater than about 10 cSt at 40° C. are desired. These fluids cool and lubricate metal surfaces, reducing friction and tool wear while removing residual metallic pieces.

Industrial Cleaning Fluids: Bio-based synthetic fluids of this technology are suitable substitutes for petroleum kerosene for use as industrial cleaners. Unlike the petroleum kerosene that can have up to 30% aromatic hydrocarbons, the bio-based synthetic fluids contain virtually no aromatics and are therefore low in toxicity and odor, and meet stringent regulatory requirements for occupational exposure.

Lubricating Base Oils: Bio-based synthetic fluids of this technology, comprising oligomerized hydrocarbons, have kinematic viscosities greater than about 10 cSt at 40° C., preferably greater than about 20 cSt at 40° C., and viscosity index values (measure of viscosity stability within operating temperature range) suitable for lube base oil applications.

Polymerization Fluids: Bio-based synthetic fluids of this technology may be used for various solution and slurry polymerization processes such as the linear low density polyethylene process. Additionally, these fluids may be used for foam blowing processes, as an environmentally friendly substitute for chlorinated hydrocarbons. Examples of such foam blowing processes include production of foamed polystyrene (e.g. STYROFOAM®) and foamed polyurethane. Isoparaffinic hydrocarbons (e.g. HDO hydroisomerization products) in the $C_5$-$C_9$ range are particularly well-suited for these applications.

Transformer Oils: Bio-based synthetic fluids of this technology are suitable for use as transformer fluids due to their low dielectric constants (from about 2 to about 3 at in the range from about 50° C. to about 200° C.) and very low water solubility. Oligomerized bio-based fluids having carbon numbers in the $C_{20}$-$C_{36}$ range are preferred due to their very high flash points.

Cosmetic Oils: Bio-based synthetic fluids of this technology may be used as ingredients in baby lotions, cold creams, ointments and cosmetics. The odorless, tasteless, and inherently non-toxic attributes of these fluids make them attractive for these applications. The fluids of this technology in the $C_{16}$-$C_{36}$ range having a kinematic viscosity greater than about 10 cSt at 40 C are particularly well-suited for use in cosmetics.

Food Preparation Oils: Bio-based synthetic fluids of this technology may be used for food contact applications. Due to their properties in preventing water absorption, and with their inherent non-toxicity and low odor, these bio-based synthetic fluids may be used to preserve wooden cutting boards, salad bowls and other wooden kitchenware/utensils. Rubbing small amounts of the oils on the wooden kitchenware fills cracks therein and prevents water/food accumulation which can lead to formation of bacteria in addition to degradation of the wooden article.

Drilling Fluids and Hydraulic Fracturing Fluids: Bio-based synthetic fluids of this technology may be used as base fluids for drilling mud applications, including for offshore applications where a good balance of thermal stability, eco-toxicity and bio-degradability is desired.

In an aspect, a method is provided which involves producing an orifice in a substrate by at least injecting a paraffinic fluid into the substrate, wherein the paraffinic fluid comprises a hydrodeoxygenated product; the hydrodeoxygenated product is produced by hydrodeoxygenating a bio-derived feed; the bio-derived feed comprising bio-derived fatty acids, fatty acid esters, or a combination thereof; the hydrodeoxygenated product comprises n-paraffins; the paraffinic fluid contains less than about 1 wt % aromatics; and the n-paraffins have a kinematic viscosity of less than about 10 cSt at 40° C. and have a biodegradability of at least about 40% after about 23 days of exposure to microorganisms. The paraffinic fluid may be any one of the compositions provided by the present technology, including, but not limited to, the oligermized product, the chlorinated product, the olefinic fluid, the HDO product, the hydroisomerized product, or mixtures of any two or more thereof. As described above, the paraffinic fluids of the present technology have flash points, thermal stabilities, viscosities, eco-toxicities and biodegradabilities excellently suited for such a method. In some embodiments, the hydrodeoxygenated product includes n-paraffins in the range of about 80 wt % to about 100 wt %; cycloparaffins in the range of about 0 wt % to about 10 wt %; and less than about 1 wt % total aromatics. In some embodiments, the paraffinic fluid further includes a hydroisomerized product produced by at least partially hydroisomerizing the hydrodeoxygenated product; wherein the hydroisomerized product comprises isoparaffins where at least about 80 wt % of the isoparaffins are mono-methyl branched paraffins; the mono-methyl branched paraffins comprise less than about 30 wt % terminal branched isoparaffins; and the isoparaffins have a kinematic viscosity of less than about 10 cSt at 40° C. and have a biodegradability of at least about 40% after about 23 days of exposure to microorganisms.

In some embodiments, the paraffinic fluid has a kinematic viscosity less than about 10 cSt at 40° C. In such embodiments, the paraffinic fluid may have a kinematic viscosity at 40° C. of about 9 cSt, about 8 cSt, about 7 cSt, about 6 cSt, about 5 cSt, about 4 cSt, about 3 cSt, about 2 cSt, about 1 cSt, and ranges in between any two of these values or below any one of these values. In some embodiments, the paraffinic fluid has a kinematic viscosity greater than about 10 cSt at 40° C. In such embodiments, the paraffinic fluid may have a kinematic viscosity at 40° C. of about 12 cSt, about 14 cSt, about 16 cSt, about 18 cSt, about 20 cSt, about 22 cSt, about 24 cSt, about 26 cSt, about 28 cSt, about 30 cSt, and ranges in between any two of these values or greater than any one of these values. In some embodiments, the paraffinic fluid has a kinematic viscosity greater than about 20 cSt at 40° C.

In some embodiments, the substrate comprises a soil substrate, a topsoil substrate, a subsoil substrate, a clay substrate, a sand substrate, a rock substrate, or a stone substrate. In some embodiments, the bio-derived fatty acids, fatty acid esters, or a combination thereof comprises algae oils, beef tallow, camelina oil, canola oil, rapeseed oil, castor oil, choice white grease, coconut oil, coffee bean oil, corn oil, cottonseed oil, fish oils, hemp oil, Jatropha oil, linseed oil, mustard oil, palm oil, palm kernel oil, poultry fat, soybean oil, sunflower oil, tall oil, tall oil fatty acid, Tung oil, used cooking oils, yellow grease, products of the food industry, or combinations of any two or more thereof. In some embodiments, the bio-derived fatty acids, fatty acid esters, or a combination thereof comprise soybean oil, corn oil, cottonseed oil, canola oil, coconut oil, sunflower oil, palm oil, palm kernel oil, rapeseed oil, or a combination of any two or more thereof. In some embodiments, the step of producing an orifice comprises hydraulic fracturing of the substrate with the paraffinic fluid.

Integrated Process for Production of Bio-Based Industrial Fluids: An embodiment of the inventive method for producing bio-based industrial fluids is presented in FIG. 1. Referring to FIG. 1, a bio-based feed 102 comprising fatty acids and/or fatty acid esters is combined with a compressed treat gas 104 to form reactor feed stream 106 and achieve hydrodeoxygenation (HDO) in HDO unit 110. The bio-based feed 102 comprises any one or more of the oils, fats, or greases recited earlier herein in this application. The bio-based feed 102 and treat gas 104 are pumped and compressed respectively to a pressure within the range described earlier herein.

The treat gas 104 for the HDO reaction is a hydrogen-rich gas, with a hydrogen concentration in the range of about 70 mol % to about 100 mol %. In some embodiments, the hydrogen concentration is between about 82 mol % and about 99 mol %. The main impurities present in the treat gas 104 include methane, ethane, propane, n-/iso-butane, hydrogen sulfide, carbon monoxide, carbon dioxide, ammonia, and water.

The HDO unit 110 comprises a preheater to raise the temperature of reactor feed 106 to achieve HDO reactor operation within the temperature range described previously in the application. In addition to the preheater, the HDO unit 110 includes an HDO reactor, separator drums/vessels, and a product stripper. The drums/vessels separate a water byproduct 112 and an HDO gas 114 from HDO product 116. The product stripper is employed for removal of residual byproduct ammonia, hydrogen sulfide, and carbon oxides, dissolved in the HDO product 116. The HDO product 116 is a paraffinic hydrocarbon composition comprising n-paraffins in the $C_{15}$-$C_{18}$ range, with elemental sulfur and elemental nitrogen less than about 5 wppm and elemental oxygen less than about 0.1 wt %. In some embodiments, elemental sulfur and elemental nitrogen are less than 1 wppm in the paraffinic hydrocarbon composition. In some embodiments, the HDO product 116 is partially recycled to the HDO reactor as a solvent/diluent for bio-based feed 102.

The HDO gas 114, containing same byproducts in addition to light hydrocarbons such as methane and propane, is optionally subjected to treatment (e.g. scrubbing with a solvent, water, or caustic/amine solutions) to reduce the concentration of these molecules in the gas 114. In some embodiments, the gas 114 is partially recycled to the HDO reactor.

The HDO product 116 is combined with treat gas 118 to form a hydroisomerization unit feed 119. The treat gas is a hydrogen-rich gas stream having the specifications of treat gas 104, but preferably containing less than about 10 ppm hydrogen sulfide, ammonia, or carbon monoxide. If needed, the HDO product 116 and treat gas 118 are pressurized/compressed to a value within the hydroisomerization operating pressure range specified earlier in this application.

The hydroisomerization unit 120 comprises a feed preheater, a hydroisomerization reactor, and separation drums for separating the hydroisomerization product 124 from the hydroisomerization gas 122. The hydroisomerization gas 122 may contain light hydrocarbons formed in the hydroisomerization reactor via hydrocracking side reactions therein.

The preheater in the hydroisomerization unit 120 raises the temperature of the feed for operating the hydroisomerization reactor within the temperature range indicated earlier in this application.

The hydroisomerization gas 122 is combined with the treat gas 104 and/or the treat gas 118, via a compression stage if desired.

The hydroisomerization product 124, comprising paraffinic hydrocarbons in the $C_5$-$C_{18}$ range, is directed to oligomerization unit 130, where it is combined with an organic peroxide initiator 126 according to conditions and limitations provided previously. In embodiments where a batch oligomerization reactor is employed, the oligomerization unit 130 is equipped with a plurality of feed tanks. In these embodiments, one tank is used to charge the oligomerization reactor while the other is being filled with hydroisomerization product 124. The oligomerization effluent 132 includes both oligomerized and unconverted components of hydroisomerization product 124. As such, the oligomerization effluent 132 is a paraffinic hydrocarbon composition in the $C_5$-$C_{37}$+ range, characterized by a high degree of $C_2$+ chain branching.

The oligomerization effluent is directed to a fractionation unit 140. The fractionation unit may be one distillation column with side draws, or a plurality of columns operating at different pressures. Therein the oligomerization effluent is fractionated into Fraction 142 comprising hydrocarbons in the $C_5$-$C_{15}$ range, Fraction 144 comprising hydrocarbons in the $C_{16}$-$C_{18}$ range, and Fraction 146 comprising hydrocarbons in the $C_{19}$-$C_{37}$+ range. Fraction 144 may be used for solvents, drilling fluids, hydraulic fracturing fluids, and other industrial fluid applications where kinematic viscosity values are less than about 10 cSt at 40° C. Fraction 146 may be used for lubricating oils, dielectric fluids, grain de-dusting fluids, mineral oil, and other applications where the kinematic viscosity is greater than about 10 cSt at 40 C. In some embodiments, it is necessary to further fractionate the fluid fraction comprising $C_{37}$+ fractions in order to meet the maximum boiling temperature specified for the fluid.

Fraction 142 may be partially or completely recycled to oligomerization unit 130. Alternatively, Fraction 142 may be further fractionated into a $C_5$-$C_9$ ranged and $C_{10}$-$C_{15}$ ranged fractions for use as other solvents or fuels. The fluid fractions are preferably additized with an anti-oxidant, and other additives specific to the application, before drumming and shipping. The anti-oxidant is preferably a hindered phenol introduced at a concentration between about 2 and about 200 wppm. In some embodiments, the anti-oxidant is at a concentration between about 10 wppm and about 100 wppm.

The present invention, thus generally described, will be understood more readily by reference to the following examples, which are provided by way of illustration and are not intended to be limiting of the present invention.

EXAMPLES

Example 1

Demonstration of the Bio-Degradability of a Bio-Based Synthetic Hydrocarbon Fluids Canola oil was hydrodeoxygenated in a 100 cc tubular reactor packed with 20 cc Mo catalyst (top layer) and 80 cc NiMo catalyst (bottom layer) and then pressurized to 1600 psig with hydrogen. The catalysts were commercially available products obtained in oxide form. The catalysts were sulfided in the reactor using dimethyl disulfide (DMDS), following a ramp-hold temperature profile. The first hold was 12 hrs at 400° F. (wherein $H_2S$ breakthrough was confirmed), and the second hold was about 10 hrs at 700° F. The temperatures were lowered to about 450° F. before introduction of 100% canola oil (spiked with 100 ppm sulfur as DMDS). After a break-in period of partial hydrodeoxygenation, the reactor temperature was raised to 640 F. The liquid hourly space velocity of canola oil was maintained at 1 vol/vol/hr, along with a 10,000 SCF/Bbl gas-to-oil ratio.

The canola oil feed and HDO product were both analyzed for elemental oxygen. The feed was 11.1 wt % oxygen whereas the HDO product was below detection limit (<0.1 wt % oxygen). The HDO product had a flash point of 138° C., a viscosity of 3.68 cSt at 40° C., and density of 0.800 kg/L.

The HDO product was subjected to biodegradability test according to ASTM D5864-05. After 23 days of exposure to microorganisms at the conditions specified in the test method, with room temperature in the 20-25° C. range, the paraffinic HDO product degradation as measured by $CO_2$ production was found to be 44.2%. By comparison, the biodegradability of poly alpha olefins is reported to be in the 0-25% range.

Example 2

Hydroisomerized HDO Product Fractions

HDO paraffins were hydroisomerized (HI) according to the conditions described in this technology, using a Pt/Pd-on-amorphous silica/alumina catalyst. The hydroisomerized products were fractionated into different cuts using both laboratory as well as commercial scale distillation columns. The fractionation cuts' boiling ranges corresponded to commercial grades of petroleum-based paraffinic fluids such as ISOPAR® L, ISOPAR® M, ISOPAR® V, SOLTROL® 170, and SOLTROL® 220. The results are summarized in Table 1.

TABLE 1

Comparison of Bio-Based Isoparaffin Fluid Fractions (HI Cuts) to Commercial Petro-Solvents

| | ISOPAR GRADE | | | | | | | | |
|---|---|---|---|---|---|---|---|---|---|
| | L | | M | | | V | | | |
| | ISOPAR and Equivalent Products | | | | | | | | |
| | ISOPAR | HI Cut 2 | ISOPAR | SOL-170 | HI Cut 3 | ISOPAR | SOL-220 | HI Cut 4 | HI BTMS |
| Solvency | | | | | | | | | |
| Kauri-butanol value, ASTM D1133 | 27 | 25 | 25 | 24.6 | 23 | 23 | NA[3] | 20.5 | 19 |
| Aniline Point (° C.) | 85 | 80 | 91 | 91 | 86 | 92 | NA | 94 | 98 |
| Volatility | | | | | | | | | |
| Flash Point, ASTM D56 (° C.) | 64 | 60 | 93 | 87 | 87 | 129 | 100 | 121 | 124 |
| Distillation, ASTM D86 IBP (° C.) | 189 | 165 | 223 | ≥216 | 198 | 273 | ≥218 | 228 | 273 |
| Distillation, ASTM D86 EP (° C.) | 207 | 209 | 254 | ≤246 | 243 | 312 | ≤315 | 281 | 304 |
| Specific Gravity @ 15.6 C., ASTM D1250 | 0.77 | 0.77 | 0.79 | 0.78 | 0.77 | 0.83 | NA | 0.78 | 0.784 |
| Composition, wt % | | | | | | | | | |
| Saturates | 99.9 | >99 | 99.9 | | >99 | 99.8 | NA | >99 | 99.7 |
| Aromatics | <0.01 | <1 | <0.05 | 0.01 | <1 | <0.5 | NA | <1 | 0.3 |

Notes:
1. ISOPAR is a trademark of ExxonMobil Chemical
2. SOLTROL ("SOL") is a trademark of Chevron Phillips Chemical
[3] NA = Data not available As observed in Table 1, the bio-based fluids, HI Cuts 2-4 and HI Btms, have the desired selective solvency for use as industrial solvents: Kauri-Butanol values greater than about 19, and aniline points greater than about 80° C.

The HI Btms fraction was further analyzed for comparison with two commercial petroleum-based drilling fluids, recognized for their relatively low ecotoxicity, high flash points, and low pour points. These products are offered for offshore applications. Table 2 provides a summary of the results.

TABLE 2

Comparison of Bio-Based Isoparaffinic Fluid (HI Btms) to Commercial Petro-Based Drilling Fluids

| Property | CLAIRSOL NS[a] | ESCAID 120[b] | HI Btms |
|---|---|---|---|
| Specific Gravity | 0.82 | 0.818 | 0.784 |
| Flash Point, ° C. | 122 | 101 | 124 |
| Pour Point, ° C. | −18 | −24 | <−12 |
| Aromatics, wt % | <0.5 | 0.9 | <0.5 |
| Viscosity at 20° C., cSt | | | |
| Viscosity at 40° C., cSt | 3.4 | 2.36 | 3.49 |
| Aniline Pt., ° C. | 84 | | 98 |
| Distillation, ° C. | | | |
| IBP | 261 | 235 | 273 |
| FBP | 293 | 270 | 304 |

Notes:
[a]CLAIRSOL is tradename of Petrochem Carless, a leading supplier of drilling base fluids in Europe
[b]ESCAID is tradename of ExxonMobil Chemical, a leading supplier of drilling base fluids The table shows that the bio-based drilling fluid (or drilling mud base fluid) meets all the performance parameters presently provided by the petroleum-based drilling fluids.

Example 3

Peroxide-Initiated Oligomerization of Paraffins 100 parts by weight of a hydroisomerized HDO product is introduced to a round-bottom flask reactor equipped with a mechanical stirrer, a reflux condenser, a temperature indicator, and a heating mantle. The hydroisomerized HDO product is analyzed via gas chromatography (GC) and is found to consist mainly of $C_9$-$C_{18}$ n-paraffins and iso-paraffins. Upon reaching about 200° C., 20 parts by weight of LUPEROX 101 organic peroxide[2,5-dimethyl 2,5-di(t-butylperoxy)hexane; purchasable from Aldrich] is added in 10 equal parts over 5 hours. Upon reaching the 6$^{th}$ hour, the reactor is cooled and analyzed via GC where increase in carbon number is confirmed. The product is distilled to remove the lighter, unreacted components and the byproducts of peroxide decomposition. The higher carbon number product is then tested for biodegradability according to D5864 guidelines and expected to display at least 40+% biodegradation after 23 days of exposure to micro-organisms.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method comprising producing an orifice in a substrate by at least injecting a viscosity-altered paraffinic fluid into the substrate, wherein
the paraffinic fluid comprises a hydrodeoxygenated product and a hydroisomerized product;
the hydrodeoxygenated product is produced by hydrodeoxygenating a bio-derived feed;

the hydroisomerized product is produced by at least partially hydroisomerizing the hydrodeoxygenated product;

the bio-derived feed comprises bio-derived fatty acids, fatty acid esters, or a combination thereof;

the hydrodeoxygenated product comprises n-paraffins;

the hydroisomerized product comprises isoparaffins;

the paraffinic fluid contains less than about 1 wt % aromatics; and the n-paraffins
have a kinematic viscosity of less than about 10 cSt at 40° C.; and
have a biodegradability of at least about 40% after about 23 days of exposure to microorganisms;

the isoparaffins
are at least about 80 wt % mono-methyl branched paraffins where the mono-methyl branched paraffins comprise less than about 30 wt % terminal branched isoparaffins;
have a kinematic viscosity of less than about 10 cSt at 40° C.; and
have a biodegradability of at least about 40% after about 23 days of exposure to microorganisms.

2. The method of claim 1, wherein the substrate comprises a soil substrate, a topsoil substrate, a subsoil substrate, a clay substrate, a sand substrate, a rock substrate, or a stone substrate.

3. The method of claim 1, wherein the step of producing an orifice comprises hydraulic fracturing of the substrate with the paraffinic fluid.

4. The method of claim 1, wherein the bio-derived fatty acids, fatty acid esters, or a combination thereof comprises algae oils, beef tallow, camelina oil, canola oil, rapeseed oil, castor oil, choice white grease, coconut oil, coffee bean oil, corn oil, cottonseed oil, fish oils, hemp oil, Jatropha oil, linseed oil, mustard oil, palm oil, palm kernel oil, poultry fat, soybean oil, sunflower oil, tall oil, tall oil fatty acid, Tung oil, used cooking oils, yellow grease, products of the food industry, or combinations of any two or more thereof.

5. The method of claim 1, wherein the bio-derived fatty acids, fatty acid esters, or a combination thereof comprise soybean oil, corn oil, cottonseed oil, canola oil, coconut oil, sunflower oil, palm oil, palm kernel oil, rapeseed oil, or a combination of any two or more thereof.

6. The method of claim 1, wherein the hydrodeoxygenated product comprises
n-paraffins in the range of about 80 wt % to about 100 wt %;
cycloparaffins in the range of about 0 wt % to about 10 wt %; and
less than about 1 wt % total aromatics.

7. The method of claim 1, wherein the hydrodeoxygenated product is free of benzene.

8. The method of claim 1, wherein the mono-methyl branched paraffins comprise less than about 5 wt % terminal branched isoparaffins.

9. The method of claim 1, wherein the hydroisomerized product has a ratio of isoparaffins to normal paraffins in the range of about 1:1 to about 30:1.

10. The method of claim 1, wherein the hydroisomerized product has a ratio of isoparaffins to normal paraffins in the range of about 1:1 and about 10:1.

11. The method of claim 1, wherein the hydroisomerized product is free of benzene.

12. The method of claim 1, wherein the paraffinic fluid further comprises an olefinic fluid, an oligomerized product, a chlorinated product, or mixtures of any two or more thereof.

13. The method of claim 1, wherein the paraffinic fluid further comprises an olefinic fluid, wherein the olefinic fluid comprises
at least about 10 wt % internal olefins in the $C_{16}$ to $C_{18}$ range;
a viscosity of less than about 10 cSt at 40° C.; and
is free of benzene.

14. The method of claim 13, wherein the olefinic fluid comprises
about 50-90 wt % n-paraffins in the $C_{16}$-$C_{18}$ range;
about 10-40 wt % linear internal olefins in the $C_{16}$-$C_{18}$ range; and
about 0-10 wt % linear alpha olefins in the $C_{16}$-$C_{18}$ range.

15. The method of claim 1, wherein the paraffinic fluid further comprises an oligomerized product wherein the oligomerized product has a kinematic viscosity of at least about 10 cSt at 40° C. and is free of benzene.

16. The method of claim 15, wherein the oligomerized product has a biodegradability of at least about 40% after about 23 days of exposure to microorganisms.

17. The method of claim 15, wherein the oligomerized product is a dimer, trimer, tetramer, or a mixture of any two or more thereof.

18. The method of claim 1, wherein the paraffinic fluid is free of benzene.

19. The method of claim 1, wherein the paraffinic fluid has a kinematic viscosity of less than about 10 cSt at 40° C.

20. The method of claim 1, wherein the paraffinic fluid comprises less than 0.1 wt % total aromatics.

21. The method of claim 1, wherein the hydroisomerized product comprises a pour point of at most about −10° C.

22. The method of claim 1, wherein the paraffinic fluid comprises a kinematic viscosity of less than about 5 cSt at 40° C.

23. The method of claim 1, wherein the paraffinic fluid is free of benzene and comprises
less than about 0.5 wt % aromatics;
a kinematic viscosity of less than about 5 cSt at 40° C.; and
an olefinic fluid, wherein the olefinic fluid comprises
about 50-90 wt % n-paraffins in the $C_{16}$-$C_{18}$ range;
about 10-40 wt % linear internal olefins in the $C_{16}$-$C_{18}$ range; and
about 0-10 wt % linear alpha olefins in the $C_{16}$-$C_{18}$ range.

24. The method of claim 23, wherein the step of producing an orifice comprises hydraulic fracturing of the substrate with the paraffinic fluid.

* * * * *